US 9,718,289 B2

(12) United States Patent
Kimura

(10) Patent No.: US 9,718,289 B2
(45) Date of Patent: Aug. 1, 2017

(54) INKJET RECORDING APPARATUS

(71) Applicant: FUJIFILM Corporation, Tokyo (JP)

(72) Inventor: Yosuke Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/255,578

(22) Filed: Sep. 2, 2016

(65) Prior Publication Data

US 2017/0066262 A1    Mar. 9, 2017

(30) Foreign Application Priority Data

Sep. 3, 2015    (JP) .................................. 2015-173686

(51) Int. Cl.

| | |
|---|---|
| B41J 2/045 | (2006.01) |
| B41J 25/308 | (2006.01) |
| B41J 13/00 | (2006.01) |
| B41J 2/01 | (2006.01) |
| H04N 1/00 | (2006.01) |

(Continued)

(52) U.S. Cl.
CPC .............. *B41J 13/0009* (2013.01); *B41J 2/01* (2013.01); *B41J 2/16579* (2013.01); *B41J 11/0095* (2013.01); *B41J 25/308* (2013.01); *B65H 7/14* (2013.01); *H04N 1/00013* (2013.01); *B41J 2025/008* (2013.01); *B65H 2553/412* (2013.01); *G01N 2021/8663* (2013.01)

(58) Field of Classification Search
CPC .............. B41J 2/04556; B41J 2025/008; B41J 2/16579; B41J 2/01; B41J 13/0009; B41J 11/0035; B41J 11/0095; B41J 25/308; B41J 29/393; B65H 7/14; B65H 2553/412; G01N 2021/8663
See application file for complete search history.

(56) References Cited

U.S. PATENT DOCUMENTS

| | | | |
|---|---|---|---|
| 8,419,144 B2* | 4/2013 | Castillo ............... | B41J 11/0035 347/16 |
| 2014/0054845 A1 | 2/2014 | Morikawa et al. | |
| 2016/0136949 A1* | 5/2016 | Kojima ............... | B41J 2/04503 347/8 |

FOREIGN PATENT DOCUMENTS

| | | |
|---|---|---|
| JP | 2006-084595 A | 3/2006 |
| JP | 2006-298606 A | 11/2006 |

(Continued)

OTHER PUBLICATIONS

Extended European Search Report, dated Feb. 14, 2017, for corresponding European Application No. 16186833.6.

*Primary Examiner* — Thinh H Nguyen
(74) *Attorney, Agent, or Firm* — Birch, Stewart, Kolasch & Birch, LLP

(57) ABSTRACT

An inkjet recording apparatus includes: a paper floating detecting unit which detects floating of a paper sheet at a first position; an ink jet recording unit which records an image on the paper sheet at a second position on a downstream side of the first position; and an image reader which reads the image on the paper sheet at a third position on the downstream side of the second position. When the floating is detected by the paper floating detecting unit, the image in a fixed front and rear range of the paper sheet is read by the image reader with a position where the floating is detected as a reference. The read image is displayed on a display device. An operator confirms the image displayed on the display device, and discriminates the type of the generated floating.

13 Claims, 36 Drawing Sheets

(51) Int. Cl.
  *B41J 2/165* (2006.01)
  *B41J 11/00* (2006.01)
  *B65H 7/14* (2006.01)
  *G01N 21/86* (2006.01)
  *B41J 25/00* (2006.01)

(56) References Cited

FOREIGN PATENT DOCUMENTS

| | | | |
|---|---|---|---|
| JP | 2007-301920 A | 11/2007 | |
| JP | 2010-076872 A | 4/2010 | |
| JP | 2012-143944 A | 8/2012 | |
| JP | 2015-037982 A | 2/2015 | |

\* cited by examiner

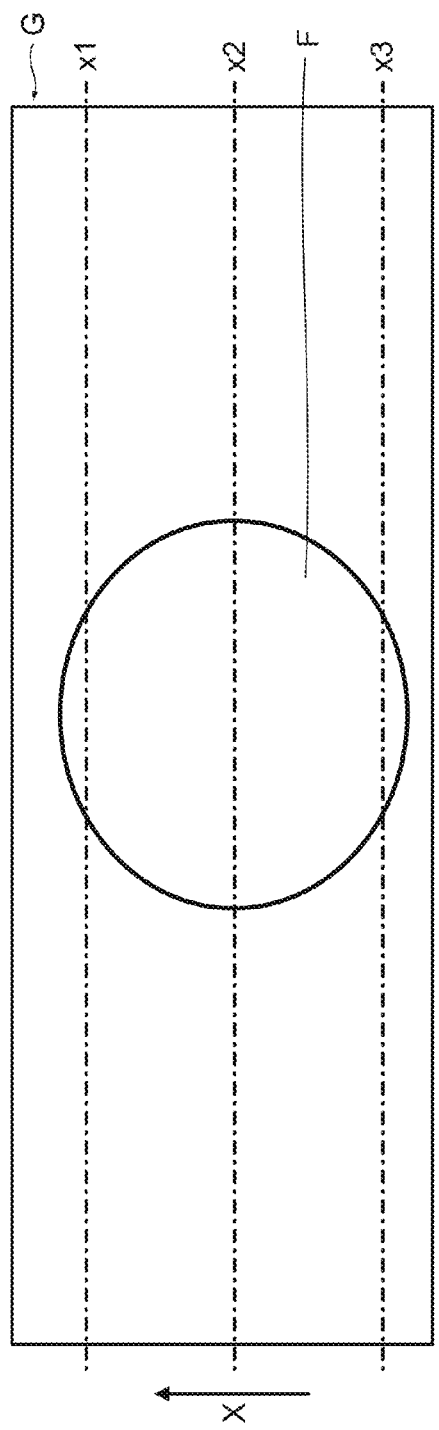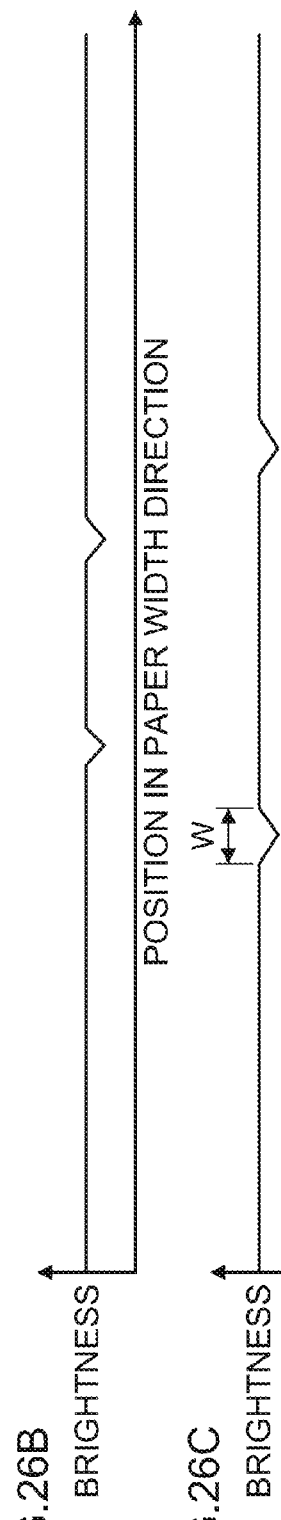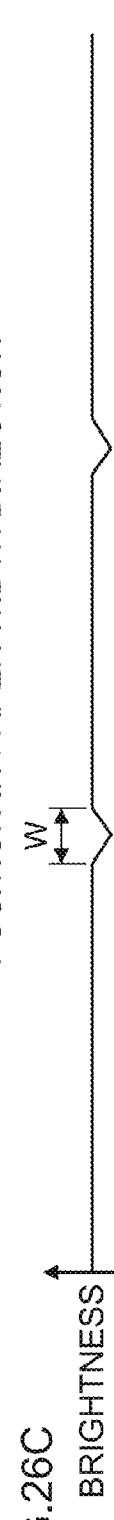
FIG.26A
FIG.26B
FIG.26C
FIG.26D

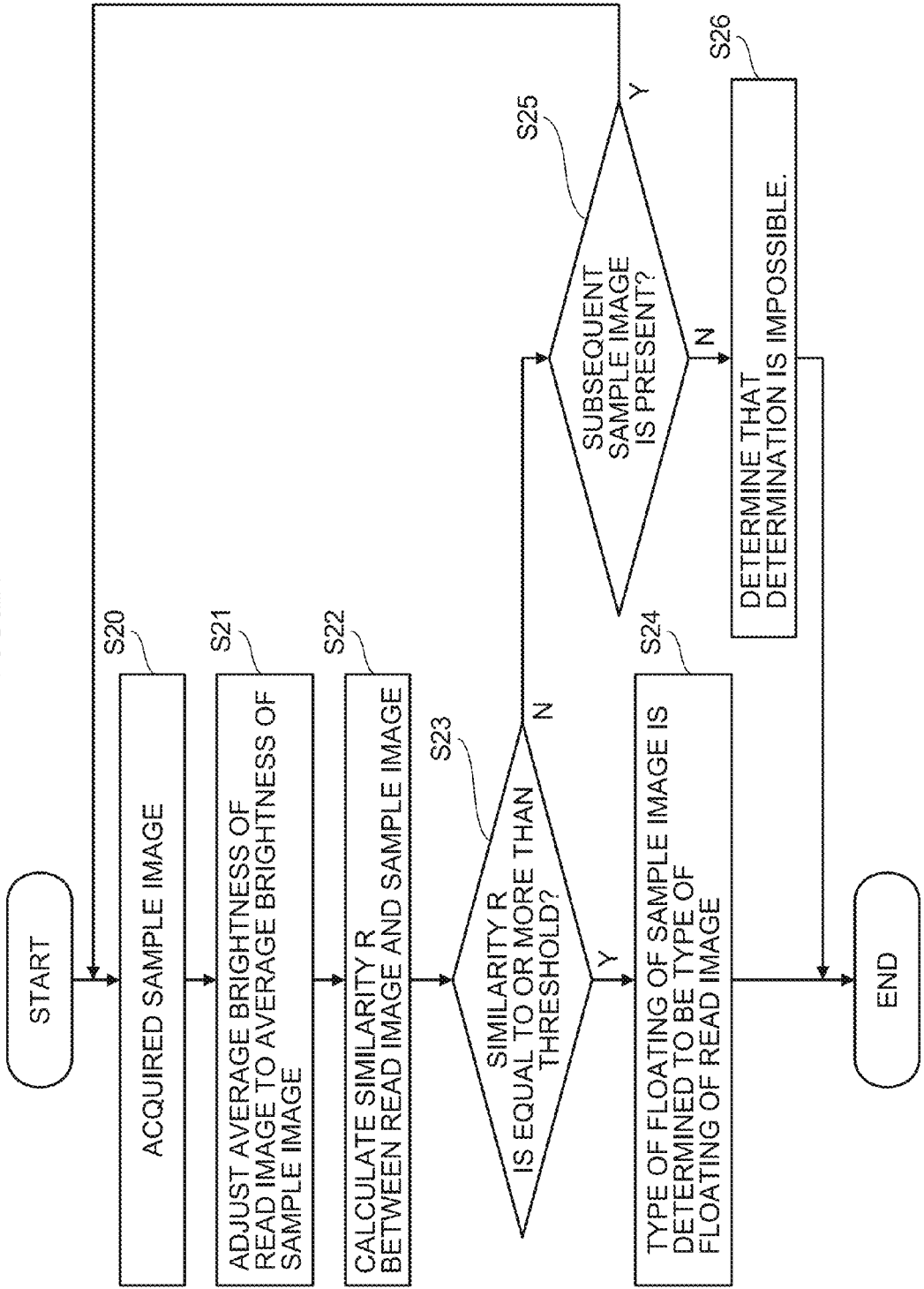

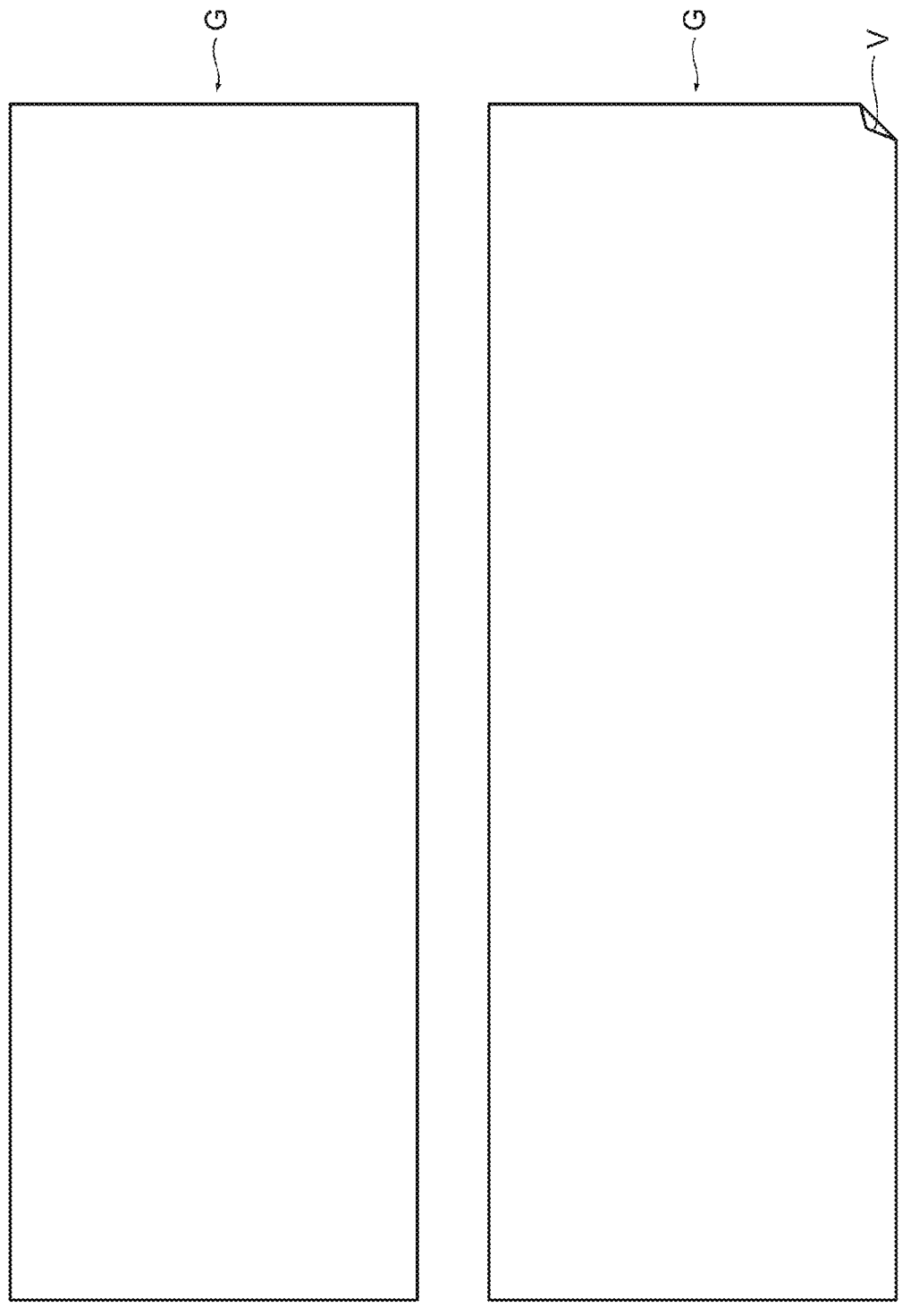

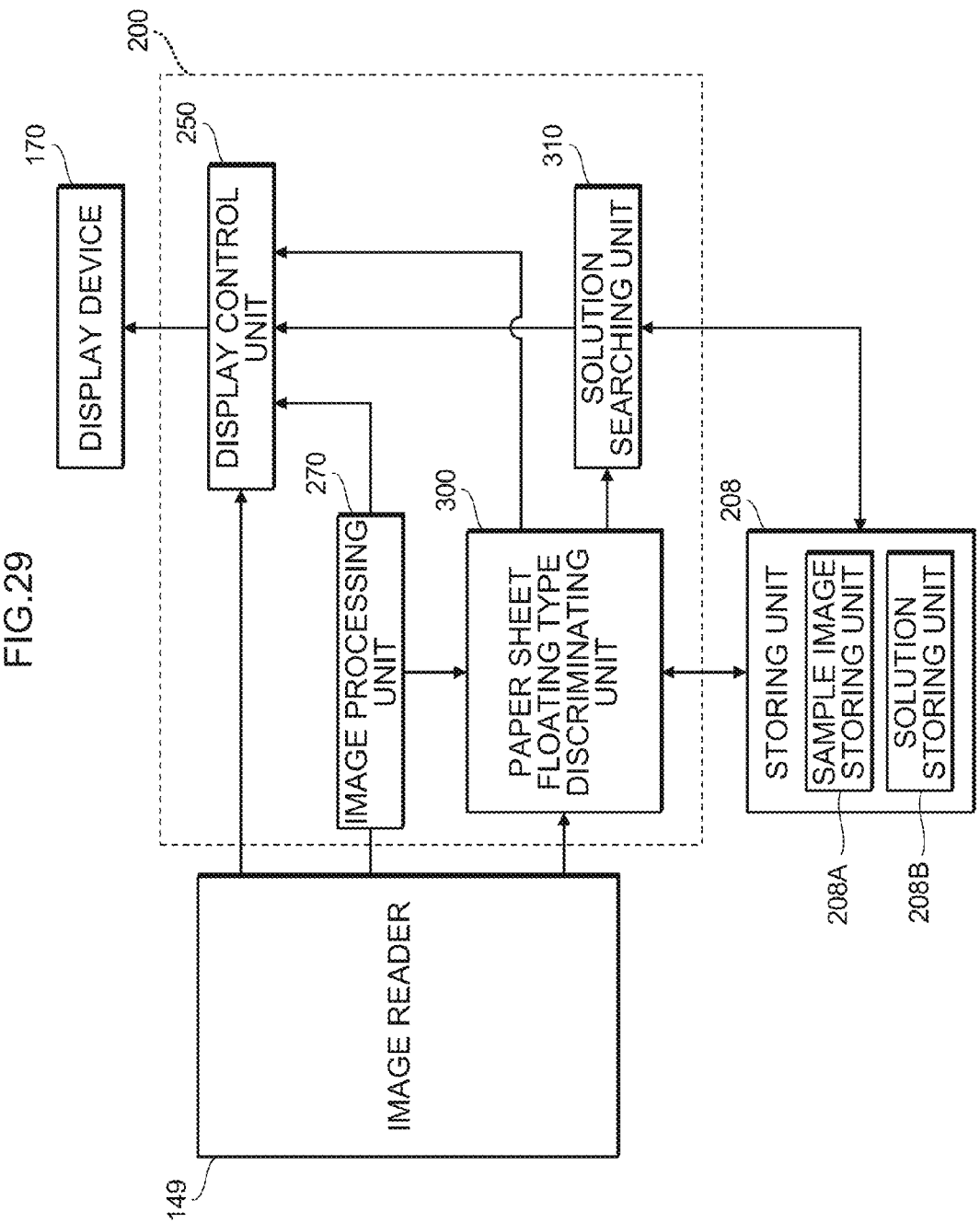

FIG.30

| TYPE OF FLOATING | SOLUTION |
|---|---|
| LONGITUDINAL WRINKLE | (1) ADJUST POSITION OF RUNNER WHEEL<br>(2) ADJUST POSITION OF RETAINER<br>(3) INCREASE AIR VOLUME OF BLOWER OF PAPER FEEDER<br>(4) DECREASE PRESSURE OF PAPER PRESSING ROLLER<br>(5) CONFIRM BACK TENSION PRESSURE IS IN STIPULATED RANGE<br>(6) DECREASE SUCKING PRESSURE OF INKJET RECORDING DRUM |
| ANNULAR WRINKLE | INCREASE SUCKING PRESSURE OF INKJET RECORDING DRUM |
| FOLDING | INCREASE SUCKING PRESSURE OF INKJET RECORDING DRUM |

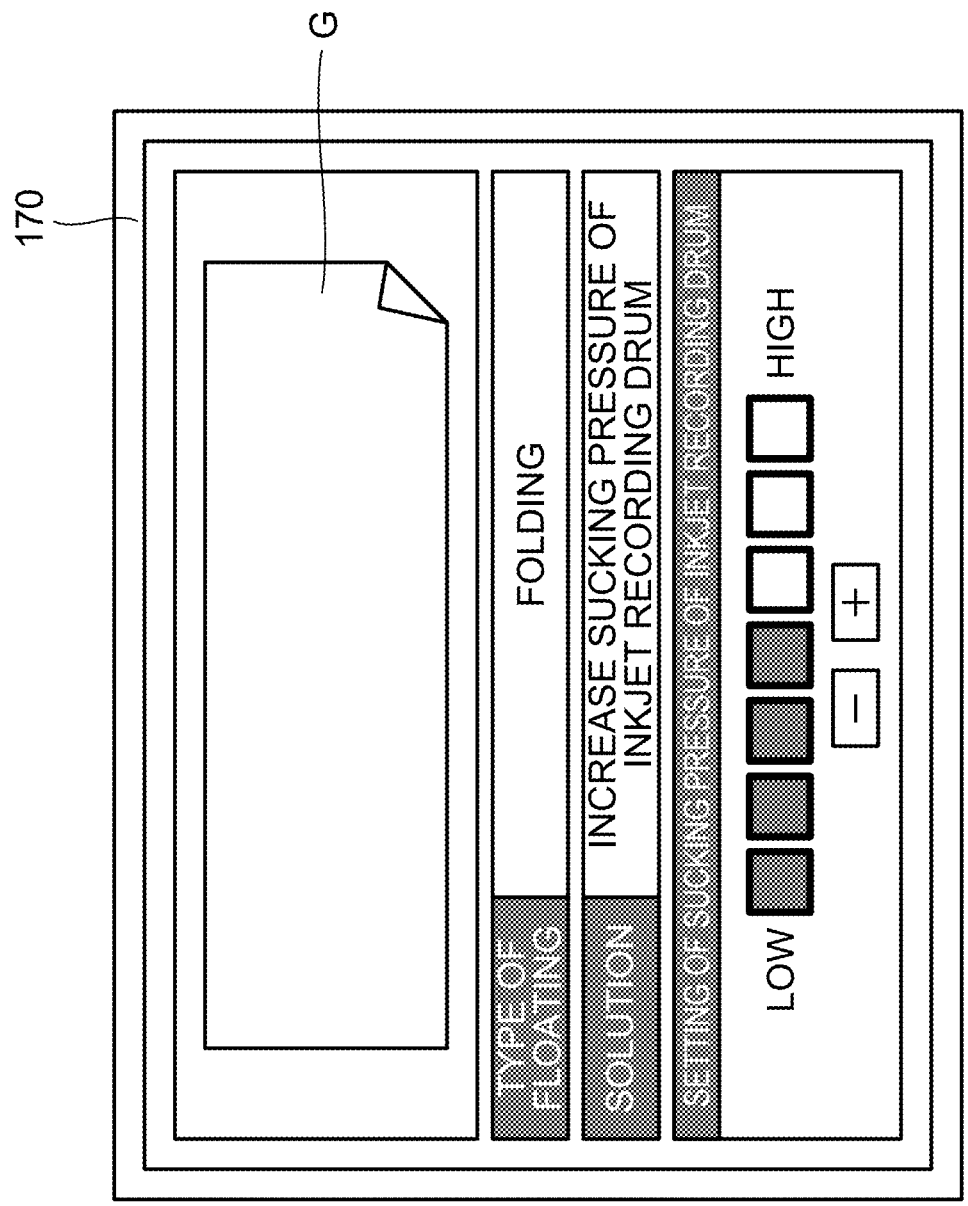

INKJET RECORDING APPARATUS

CROSS-REFERENCE TO RELATED APPLICATIONS

The present application claims priority under 35 U.S.C. §119 to Japanese Patent Application No. 2015-173686, filed on Sep. 3, 2015. The above application is hereby expressly incorporated by reference, in its entirety, into the present application.

BACKGROUND OF THE INVENTION

Field of the Invention

The present invention relates to an inkjet recording apparatus which records an image on a paper sheet conveyed through a fixed conveying path by an inkjet method.

Description of the Related Art

In the inkjet recording apparatus, paper sheets need to be conveyed in a flat state. When floating, such as wrinkles and folding, is present in a paper sheet, not only may image quality deteriorate, but also the paper sheet may contact inkjet heads, and the inkjet heads may be damaged in the worst case.

Accordingly, in conventional inkjet recording apparatuses, floating of the paper sheet is detected on the upstream side of an inkjet recording unit. When the detected floating is equal to or more than a fixed level, conveyance of the paper sheet is stopped to prevent the paper sheet from contacting the inkjet heads (see, for example, Japanese Patent Application Laid-Open No. 2010-076872). When conveyance of the paper sheet is stopped, an operator visually confirms a floating generation status and performs adjustment of a paper feeding system or a conveyance system in accordance with the type of the generated floating.

However, when conveyance of the paper sheet is stopped, it causes not only a problem that the paper sheet currently under recording is wasted, but also a problem that paper sheets under preprocessing and post-processing within the apparatus are wasted. Moreover, once the conveyance is stopped, restarting takes time so that productivity also deteriorates.

As a solution to such problems, there is known a technique of retreating the inkjet heads to prevent the paper sheet from contacting the inkjet heads when floating is generated in the paper sheet (see, for example, Japanese Patent Application Laid-Open No. 2012-143944). The solution presents an effect that can suppress generation of waste sheets to a minimum.

However, when conveyance of the paper sheet is continued, it becomes impossible to confirm the floating generation status, which causes a situation in which necessary adjustment cannot be performed.

To cope with this situation, techniques of reading the surface of a paper sheet with a scanner and analyzing the obtained image to detect wrinkles and the like generated in the paper sheet are disclosed in Japanese Patent Laid-Open No. 2007-301920, Japanese Patent Application Laid-Open No. 2006-084595, Japanese Patent Application Laid-Open No. 2015-037982, and Japanese Patent Application Laid-Open No. 2006-298606.

SUMMARY OF THE INVENTION

However, the techniques disclosed in Japanese Patent Laid-Open No. 2007-301920, Japanese Patent Application Laid-Open No. 2006-084595, Japanese Patent Application Laid-Open No. 2015-037982, and Japanese Patent Application Laid-Open No. 2006-298606 need to read an entire paper sheet and to analyze the entire paper sheet, which is disadvantageous in the point that a processing load in each paper sheet is large. Hence, the techniques disclosed in Japanese Patent Laid-Open No. 2007-301920, Japanese Patent Application Laid-Open No. 2006-084595, Japanese Patent Application Laid-Open No. 2015-037982, and Japanese Patent Application Laid-Open No. 2006-298606 have a disadvantage that consecutive processing of the paper sheets causes deteriorated processing speed.

Furthermore, when recording of an image is stopped halfway, it is extremely difficult to detect wrinkles and the like from the read image. More specifically, when a pattern of the image is recorded halfway, it is extremely difficult to distinguish the wrinkles and the like from the pattern. To execute processing by excluding a pattern part, it is still necessary to determine the range of the pattern, so that the processing takes great time.

The present invention has been made in consideration of such circumstances, and it is therefore an object of the present invention to provide an inkjet recording apparatus which can easily identify the type of floating when the floating is generated in a paper sheet during conveyance.

Solutions to the above problems are as described below:

(1) An inkjet recording apparatus, including: a conveying device which conveys a paper sheet along a fixed conveying path; a paper sheet floating detecting device which detects floating of the paper sheet conveyed by the conveying device at a first position set on the conveying path; an ink jet recording device which records an image on the paper sheet conveyed by the conveying device at a second position set on a downstream side of the first position; an image reading device which reads, line by line, the image of the paper sheet conveyed by the conveying device at a third position set on the downstream side of the second position; and an image reading control unit which makes the image reading device read the image in a fixed range along a conveyance direction of the paper sheet when the floating of the paper sheet is detected by the paper sheet floating detecting device, the image being read with a position where the floating is detected as a reference.

According to the present aspect, when floating of a paper sheet is detected by the paper sheet floating detecting device, an image in a fixed range along the conveyance direction of the paper sheet is read by the image reading device with the position where floating is detected as a reference. That is, only the image in a region where the floating is generated is read. This makes it possible to reduce an operation load in reading operation. Since only the image in the region where the floating is generated is read, the floating can easily be identified based on the image, and the type of the floating can also easily be identified.

(2) The inkjet recording apparatus according to the aspect (1), wherein when the floating of the paper sheet is detected by the paper sheet floating detecting device, the image reading control unit makes the image reading device read the image in a fixed front and rear range in the conveyance direction of the paper sheet with the position where the floating is detected as a reference.

According to the present aspect, when the floating of the paper sheet is detected by the paper sheet floating detecting device, the image in the fixed front and rear range in the conveyance direction of the paper sheet is read by the image reading device with the position where the floating is detected as a reference. This makes it possible to read from the paper sheet the image in a region where the floating is generated.

(3) The inkjet recording apparatus according to the aspect (1), wherein when the floating of the paper sheet is detected by the paper sheet floating detecting device, the image reading control unit makes the image reading device read the image in a fixed rear range in the conveyance direction of the paper sheet with the position where the floating is detected as a reference.

According to the present aspect, when the floating of the paper sheet is detected by the paper sheet floating detecting device, the image in the fixed rear range in the conveyance direction of the paper sheet is read by the image reading device with the position where the floating is detected as a reference. This makes it possible to read from the paper sheet the image in a region where the floating is generated.

(4) The inkjet recording apparatus according to any one of the aspects (1) to (3), further including: a display device; and a display control unit which makes the display device display the image read by the image reading device.

According to the present aspect, the image read by the image reading device is displayed on the display device. An operator can identify the type of the floating generated in the paper sheet by visually confirming the display of the display device. In this case, since only the image in a region where the floating is generated is displayed on the display device, the floating can easily be identified, and the type of the floating can also easily be identified.

(5) The inkjet recording apparatus according to any one of the aspects (1) to (3), further including: an image processing unit which applies processing of emphasizing the floating generated in the paper sheet to the image read by the image reading device; a display device; and a display control unit which makes the display device display the image processed by the image processing unit.

According to the present aspect, when an image is read by the image reading device, the processing of emphasizing floating is applied to the image. The image subjected to the emphasis processing is then displayed on the display device. The operator can identify the type of the floating generated in the paper sheet by visually confirming the display of the display device. Since the floating of the image is emphasized and displayed, the floating can easily be identified, and the type of the floating can also easily be identified.

(6) The inkjet recording apparatus according to any one of the aspects (1) to (3), further including: a paper sheet floating type discriminating unit which analyzes the image read by the image reading device to discriminate a type of the floating generated in the paper sheet; a display device; and a display control unit which makes the display device display information on the type of the floating discriminated by the paper sheet floating discriminating unit.

According to the present aspect, the type of the floating generated in the paper sheet is analyzed based on the image read by the image reading device, and the result thereof is displayed on the display device. The operator can know the type of the floating generated in the paper sheet by visually confirming the display of the display device.

(7) The inkjet recording apparatus according to any one of the aspects (1) to (3), further including: a paper sheet floating type discriminating unit which analyzes the image read by the image reading device to discriminate a type of the floating generated in the paper sheet; a solution storing unit which stores information on a solution to each type of the floating generated in the paper sheet; a solution searching unit which searches for the solution corresponding to the type of the floating discriminated by the paper sheet floating type discriminating unit with reference to the information stored in the solution storing unit; a display device; and a display control unit which makes the display device display information on the solution searched for by the solution searching unit.

According to the present aspect, the type of the floating generated in the paper sheet is analyzed based on the image read by the image reading device, and the solution therefor is further searched for. Then, the search result is displayed on the display device. The operator can know the solution to the floating by confirming the display of the display device.

(8) The inkjet recording apparatus according to any one of the aspects (1) to (3), further including: a paper sheet floating type discriminating unit which analyzes the image read by the image reading device to discriminate a type of the floating generated in the paper sheet; a solution storing unit which stores information on a solution to each type of the floating generated in the paper sheet; a solution searching unit which searches for the solution corresponding to the type of the floating discriminated by the paper sheet floating type discriminating unit with reference to the information stored in the solution storing unit; and an adjusting device which automatically adjusts feed and/or conveyance of the paper sheet based on the solution searched for by the solution searching unit.

According to the present aspect, the type of the floating generated in the paper sheet is analyzed based on the image read by the image reading device, and the solution therefor is further searched for. Then, the feed and/or conveyance of the paper sheet are automatically adjusted based on the search result. This makes it possible to cope with the floating of the paper sheet without human assistance.

(9) The inkjet recording apparatus according to any one of the aspects (6) to (8), further including a sample image storing unit which stores a sample image for each type of the floating generated in the paper sheet, wherein the paper sheet floating type discriminating unit discriminates the type of the floating generated in the paper sheet by pattern matching with the sample images stored in the sample image storing unit.

According to the present aspect, the type of the floating generated in the paper sheet is discriminated by a pattern matching technique.

(10) The inkjet recording apparatus according to any one of the aspects (6) to (8), wherein the paper sheet floating type discriminating unit discriminates the type of the floating generated in the paper sheet based on brightness change in the image in a paper width direction, the image being read by the image reading device.

According to the present aspect, the type of the floating generated in the paper sheet is discriminated utilizing information on the brightness change in the image in the paper width direction. That is, since the brightness of a portion where the floating is generated varies in the paper width direction depending on the type of the floating, the type of the floating is discriminated by utilizing the information on the brightness change in the paper width direction.

(11) The inkjet recording apparatus according to any one of the aspects (1) to (10), further including: a forward/backward moving device which moves the ink jet recording device forward and backward; and a forward/backward movement control unit which controls the forward/backward moving device to retreat the ink jet recording device when the floating of the paper sheet is detected by the paper sheet floating detecting device.

According to the present aspect, the ink jet recording device is configured to be movable in forward and backward directions, and when floating of the paper sheet is detected, the ink jet recording device is retreated. As a consequence, even when conveyance is continued after the floating is detected, it becomes possible to avoid the situation where the paper sheet contacts the ink jet recording device.

(12) The inkjet recording apparatus according to the aspect (11), wherein when the floating of the paper sheet is no longer detected by the paper sheet floating detecting device after the ink jet recording device is retreated, the forward/backward movement control unit returns the ink jet recording device to a position before retreat.

According to the present aspect, when the floating of the paper sheet is dissolved, the ink jet recording device is returned to the position before retreat.

(13) The inkjet recording apparatus according to any one of the aspects (1) to (12), further including an image recording stop control unit which makes the ink jet recording device stop recording of the image when the floating of the paper sheet is detected by the paper sheet floating detecting device.

According to the present aspect, when the floating of the paper sheet is detected, recording of the image is stopped. This makes it possible to prevent useless consumption of ink.

According to the present invention, when floating is generated in a paper sheet during conveyance, the type of the floating can easily be identified.

BRIEF DESCRIPTION OF THE DRAWINGS

FIGS. 26A to 26D are concept views in the case of detecting an annular wrinkle based on the brightness change;

FIG. 27 is a flow chart illustrating one example of processing procedures in the case of discriminating the type of floating by pattern matching;

FIGS. 28A and 28B illustrate a read image of a paper sheet without floating and a read image of a paper sheet with floating generated due to folding;

FIG. 29 is a functional block diagram of the computer which functions as a solution searching unit;

FIG. 30 is a table illustrating one example of a solution database;

FIG. 31 illustrates an example of a solution to the floating displayed on the display device.

DETAILED DESCRIPTION OF THE EMBODIMENTS

Hereinafter, the embodiments of the present invention are described in detail with reference to the accompanying drawings.

<<General Configuration of Inkjet Recording Apparatus>>

Figure 1:
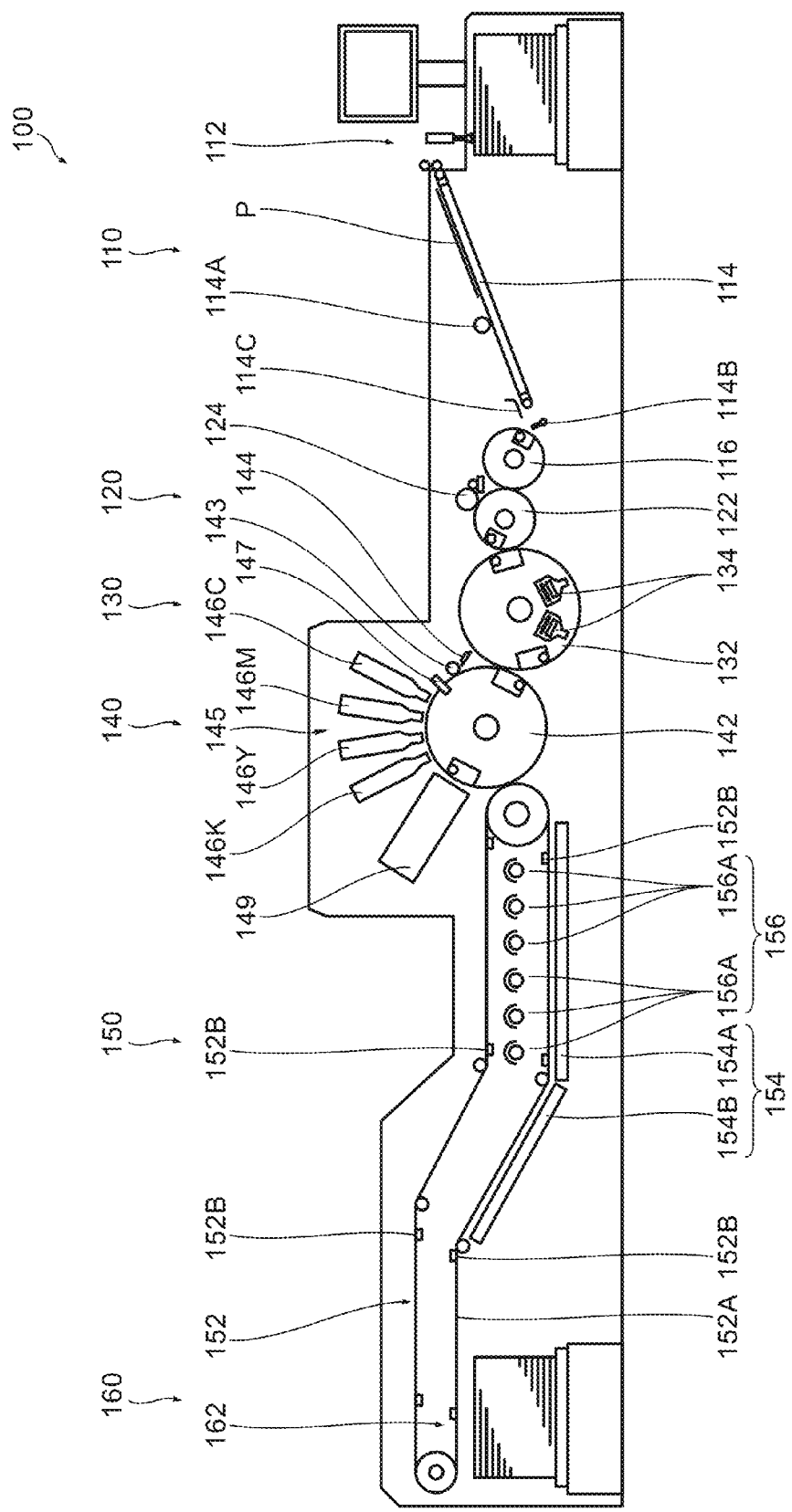
FIG. 1 is a schematic configuration view of an inkjet recording apparatus.

FIG. 1 is a schematic configuration view of an inkjet recording apparatus.

An inkjet recording apparatus 100 illustrated in FIG. 1 is a sheet-fed color inkjet recording apparatus which uses ink of four colors including cyan (C), magenta (M), yellow (Y), and black (K) to record a color image on a sheet by an inkjet method. Particularly, the inkjet recording apparatus 100 of the present embodiment is an inkjet recording apparatus which uses general-purpose printing paper as the paper sheet and water-based ink as the ink.

Here, the general-purpose printing paper does not refer to so-called inkjet dedicated paper sheets but refers to paper sheets mainly made of cellulose, such as coated paper, which are used in general offset printing machines and the like. Examples of the paper sheets include art paper, coated paper, lightweight coated paper, cast paper, and fine coated paper. The water-based ink refers to the ink made by dissolving or dispersing colorants, such as dyes and paints, into water and solvents soluble in water.

As illustrated in FIG. 1, the inkjet recording apparatus 100 includes: a paper feeding unit 110 which feeds paper sheets P; a treatment liquid coating unit 120 which coats the paper sheets P fed from the paper feeding unit 110 with a treatment liquid; a treatment liquid drying unit 130 which performs dry processing of the paper sheets P coated with the treatment liquid; an inkjet recording unit 140 which performs recording on the dry-processed paper sheets P by the inkjet method; an ink drying unit 150 which performs dry processing of the paper sheets P with an image recorded thereon; and a stacking unit 160 which stacks the dry-processed paper sheets P.

<Paper Feeding Unit>

The paper feeding unit 110 feeds the paper sheets P. As illustrated in FIG. 1, the paper feeding unit 110 includes a paper feeder 112, a feeder board 114, and a feeding drum 116.

The paper feeder 112 takes out paper sheets P, which are set at a specified position in a bundle state, one sheet at a time in order from the top sheet and feeds the taken-out paper sheets P to the feeder board 114.

In order to implement stable feeding, the paper feeder 112 includes a blower which is not illustrated. The blower blows air to the paper sheet bundle for separating the respective paper sheets P. Volume of the air blowing out of the blower is adjustable and is adjusted as necessary.

The feeder board 114 receives a paper sheet P supplied from the paper feeder 112, and feeds the paper sheet P to the feeding drum 116. The feeder board 114 includes a runner wheel 114A, a front plate 114B, and a retainer 114C.

The runner wheel 114A is a member for pressing the paper sheet P to be conveyed with the feeder board 114. The runner wheel 114A, which includes a plurality of rollers, depresses the paper sheet P with the rollers so as to press the paper sheet P to the feeder board 114. The position of the runner wheel 114A is adjustable, so that a placement position of the runner wheel 114A is adjusted as necessary.

The front plate 114B is a member for correcting the posture of the paper sheet P conveyed to an end position of the feeder board 114. When a tip of the paper sheet P conveyed to the end position of the feeder board 114 contacts the front plate 114B, the posture of the paper sheet P is corrected. The front plate 114B is driven by a motor, which is not illustrated, to oscillate and appear on a conveying path of the paper sheet P.

The retainer 114C is a member for sending the paper sheet P conveyed to the end position of the feeder board 114 to the feeding drum 116 while pressing the paper sheet P. The retainer 114C is driven by a motor, which is not illustrated, to oscillate in an anteroposterior direction, and the oscillating motions thereof depress the paper sheet P and sends the paper sheet P forward. The position of the retainer 114C is adjustable, so that a placement position of the retainer 114C is adjusted as necessary.

The feeding drum 116 receives the paper sheet P from the feeder board 114, and transports it to the treatment liquid coating unit 120. The feeding drum 116 grips and rotates the tip of the paper sheet P with a gripper provided on a peripheral surface of the feeding drum 116, so that the paper sheet P is conveyed while being wound around the peripheral surface.

The configuration of the paper feeding unit 110 is as described above. The paper sheets P are fed one sheet at a time to the feeder board 114 from the paper feeder 112, and are fed to the feeding drum 116 with the feeder board 114. Each of the fed paper sheets P is then transported to the treatment liquid coating unit 120 by the feeding drum 116.

<Treatment Liquid Coating Unit>

The treatment liquid coating unit 120 coats the paper sheet P with a treatment liquid. The treatment liquid is composed of a liquid having a function of condensing, insolubilizing, or thickening a coloring material component in the ink. By recording an image after coating the paper sheet P with such a treatment liquid, a high-definition image can be recorded even in the case where the image is recorded on general-purpose printing paper using a water-based ink.

The treatment liquid coating unit 120 includes a treatment liquid coating drum 122 which conveys the paper sheet P, and a treatment liquid coater 124 which coats a recording surface of the paper sheet P, which is conveyed by the treatment liquid coating drum 122, with the treatment liquid.

The treatment liquid coating drum 122 receives the paper sheet P from the feeding drum 116, and transports it to the treatment liquid drying unit 130. The treatment liquid coating drum 122 grips and rotates the tip of the paper sheet P with a gripper provided on a peripheral surface of the treatment liquid coating drum 122, so that the paper sheet P is conveyed while being wound around the peripheral surface.

The treatment liquid coater 124 coats the paper sheet P, which is conveyed by the treatment liquid coating drum 122, with the treatment liquid. In the present embodiment, the treatment liquid is roller-coated. That is, a roller having the treatment liquid applied to a peripheral surface thereof is pressed against the paper sheet P, which is conveyed by the treatment liquid coating drum 122, so as to coat the paper sheet P with the treatment liquid. The method for coating with the treatment liquid is not limited thereto, and other methods, such as a coating method using inkjet heads and a coating method using a spray, may also be adopted.

The configuration of the treatment liquid coating unit 120 is as described above. The paper sheet P is coated with the treatment liquid by the treatment liquid coater 124 in the process of being conveyed by the treatment liquid coating drum 122.

<Treatment Liquid Drying Unit>

The treatment liquid drying unit 130 performs dry processing of the paper sheet P coated with the treatment liquid. The treatment liquid drying unit 130 includes a treatment liquid drying drum 132 which conveys the paper sheet P, and a treatment liquid dryer 134 which blows warm air to the paper sheet P, which is conveyed by the treatment liquid drying drum 132, to dry the paper sheet P.

The treatment liquid drying drum 132 receives the paper sheet P from the treatment liquid coating drum 122 of the treatment liquid coating unit 120, and transports it to the inkjet recording unit 140. The treatment liquid drying drum 132, which is configured with a frame constructed into a cylindrical form, grips and rotates the tip of the paper sheet P with a gripper provided on a peripheral surface of the treatment liquid drying drum 132, so that the paper sheet P is conveyed while being wound around the peripheral surface.

The treatment liquid dryer 134, which is placed inside the treatment liquid drying drum 132, sends warm air toward the paper sheet P conveyed by the treatment liquid drying drum 132.

The configuration of the treatment liquid drying unit 130 is as described above. The paper sheet P is dry-processed by being exposed to the warm air sent from the treatment liquid dryer 134 in a process of being conveyed by the treatment liquid drying drum 132.

<Inkjet Recording Unit>

The inkjet recording unit 140 records a color image on the recording surface of the paper sheet P with ink of four colors including cyan (C), magenta (M), yellow (Y), and black (K).

Figure 2:
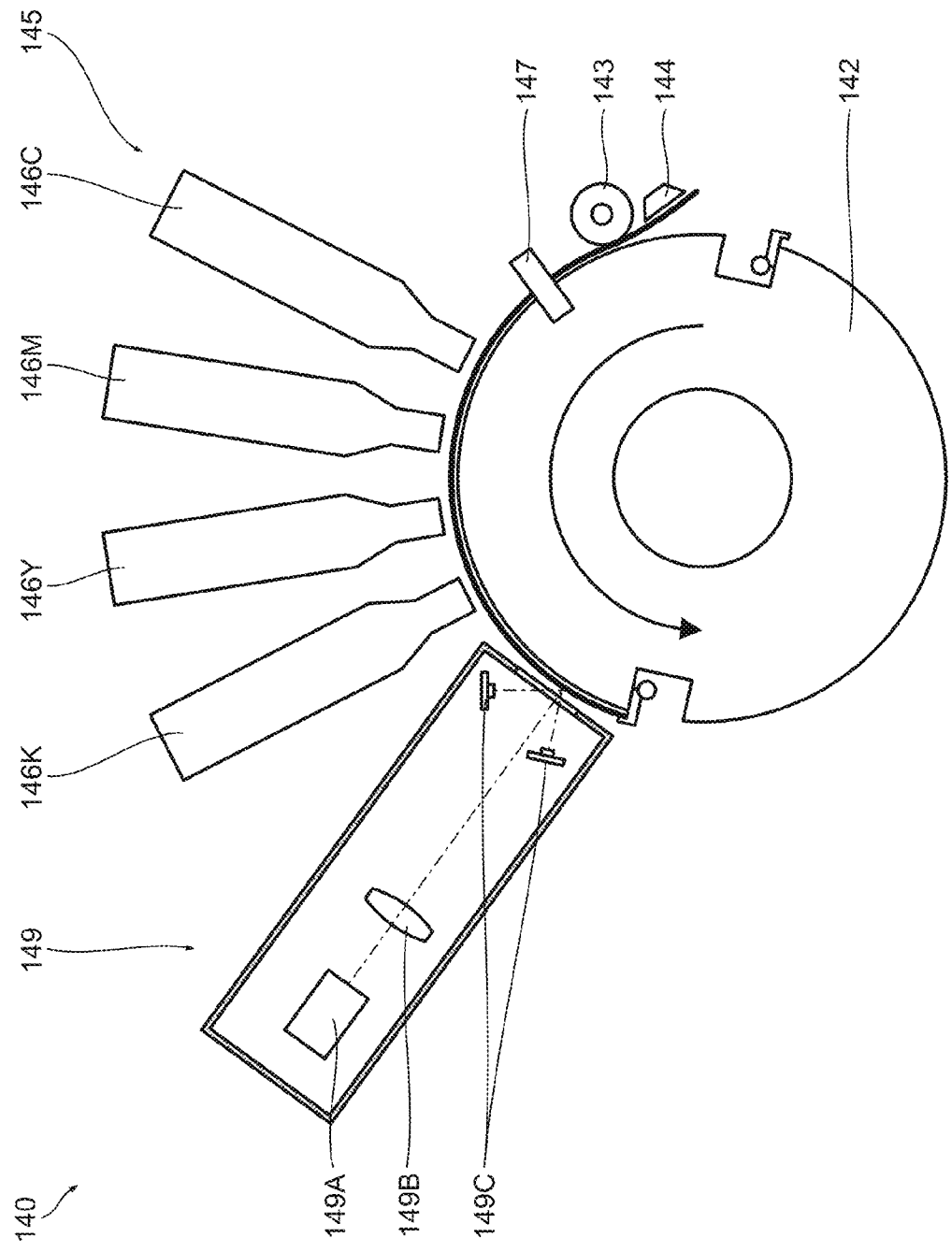
FIG. 2 is a schematic configuration view of the inkjet recording apparatus.

FIG. 2 is a schematic configuration view of the inkjet recording unit. As illustrated in FIG. 2, the inkjet recording unit 140 includes an inkjet recording drum 142 which conveys the paper sheet P along a fixed conveying path, a paper pressing roller 143 which presses the paper sheet P conveyed by the inkjet recording drum 142, a back tension applying unit 144 which applies back tension to the paper sheet P, an ink jet recording unit 145 which records an image on the paper sheet P conveyed with the inkjet recording drum 142 by the inkjet method, a paper floating detecting unit 147 which detects floating of the paper sheet P conveyed by the inkjet recording drum 142, and an image reader 149 which reads the image of the paper sheet P conveyed by the inkjet recording drum 142 line by line.

The inkjet recording drum 142 is one example of the conveying device. The inkjet recording drum 142 receives the paper sheet P from the treatment liquid drying drum 132, and transports it to the ink drying unit 150 at constant speed. The inkjet recording drum 142 grips and rotates the tip of the paper sheet P with a gripper provided on a peripheral surface of the inkjet recording drum 142, so that the paper sheet P is conveyed while being wound around the peripheral surface. Particularly, the inkjet recording drum 142 conveys the wound paper sheet P while sucking the paper sheet P to the peripheral surface. Negative pressure is utilized for suction. The inkjet recording drum 142, which includes a number of suction holes on the peripheral surface, sucks the paper sheet P through the suction holes to put the paper sheet P in close contact with the peripheral surface. In addition to negative pressure, static electricity can also be used for suction. To suck the paper sheet with static electricity, the inkjet recording drum 142 is charged.

The paper pressing roller 143 depresses the paper sheet P, which is conveyed by the inkjet recording drum 142, at a fixed position to put the paper sheet P in close contact with the peripheral surface of the inkjet recording drum 142. The paper pressing roller 143 is arranged at a position immediately behind the position where the inkjet recording drum 142 receives the paper sheet P from the treatment liquid drying drum 132. As a consequence, the paper sheet P is wound around the peripheral surface of the inkjet recording drum 142 while being depressed by the paper pressing roller 143.

The back tension applying unit 144 sucks the surface of the paper sheet P at a position immediately before the paper pressing roller 143 to apply back tension to the paper sheet P. That is, the force to pull the paper sheet P in a direction opposite to the conveyance direction is applied. In this way, the paper sheet P is wound around the inkjet recording drum 142 while being pulled in the direction opposite to the conveyance direction, which makes it possible to suppress generation of wrinkles.

The ink jet recording unit 145, which is an ink jet recording device in a broad sense, records an image on the paper sheet P at a second position set on the conveying path of the paper sheet P. The ink jet recording unit 145 includes an inkjet head 146C which ejects an ink droplet of cyan, an inkjet head 146M which ejects an ink droplet of magenta, an inkjet head 146Y which ejects an ink droplet of yellow, and an inkjet head 146K which ejects an ink droplet of black.

The inkjet heads 146C, 146M, 146Y, and 146K are integrally mounted on a carriage, which is not illustrated, to constitute the ink jet recording unit 145.

Each of the inkjet heads 146C, 146M, 146Y, and 146K is an ink jet recording device in a narrow sense. Each of the inkjet heads 146C, 146M, 146Y, and 146K records an image on the paper sheet P conveyed by the inkjet recording drum 142 with a single pass. Accordingly, the inkjet heads 146C, 146M, 146Y, and 146K are each configured with a line head corresponding to the paper sheet width of maximum-size paper sheets handled in the inkjet recording apparatus 100.

Figure 3:
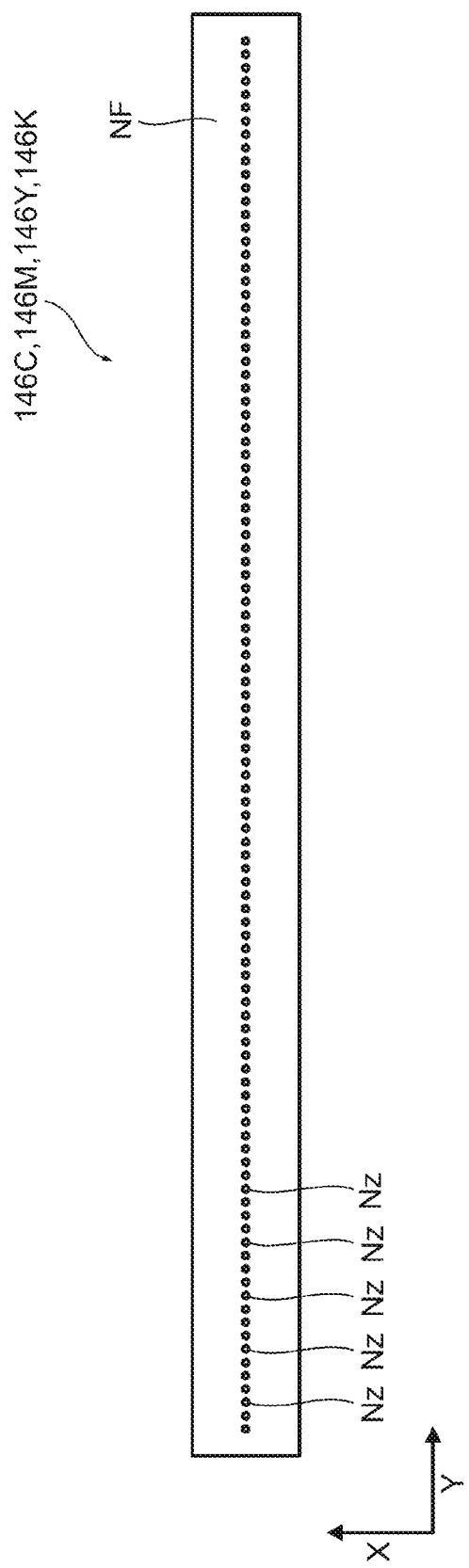
FIG. 3 is a plan view of a nozzle face.

The inkjet heads 146C, 146M, 146Y, and 146K have nozzle faces at their tips, respectively. Ink droplets are ejected from nozzles arranged on the respective nozzle faces toward the paper sheet P conveyed by the inkjet recording drum 142. FIG. 3 is a plan view of the nozzle face. As illustrated in FIG. 3, the nozzle faces NF of the inkjet heads 146C, 146M, 146Y, and 146K have nozzles Nz arranged at constant pitches along a direction Y orthogonal to the conveyance direction X of the paper sheet P.

Each of the inkjet heads 146C, 146M, 146Y, and 146K is mounted on the carriage, which is not illustrated, so as to be arranged at fixed intervals along the conveyance direction of the paper sheet P. In the inkjet recording apparatus 100 of the present embodiment in particular, each of the inkjet heads 146C, 146M, 146Y, and 146K is radially arranged around the inkjet recording drum 142.

The carriage includes a forward/backward moving mechanism which individually moves the inkjet heads 146C, 146M, 146Y, and 146K forward and backward with respect to the inkjet recording drum 142. The forward/backward moving mechanism is one example of the forward/backward moving device. By utilizing the forward/backward moving mechanism, a distance from the nozzle face of each of the inkjet heads 146C, 146M, 146Y, and 146K to the peripheral surface of the inkjet recording drum 142 can be adjusted. By adjusting the distance, a distance from the nozzle face of each of the inkjet heads 146C, 146M, 146Y, and 146K to the surface of the paper sheet can be adjusted. The distance, which is an ink flying distance, may also be called a slow distance. By utilizing the forward/backward moving mechanism, each of the inkjet heads 146C, 146M, 146Y, and 146K can be retreated in case of emergency. That is, the respective inkjet heads 146C, 146M, 146Y, and 146K can be moved to positions at a fixed height from the peripheral surface of the inkjet recording drum 142.

The carriage is movably provided along a rotation shaft of the inkjet recording drum 142. The ink jet recording unit 145 is provided to be movable between an "image recording position" set on the conveying path of the paper sheet P, and a "maintenance position" set outside the conveying path of the paper sheet P when the carriage is moved. A capping device which is not illustrated is provided at the maintenance position. During standby and power OFF states, the ink jet recording unit 145 moves to the maintenance position to be capped by the capping device.

—Paper Floating Detecting Unit—

The paper floating detecting unit 147 is one example of the paper sheet floating detecting device. The paper floating detecting unit 147 detects floating of the paper sheet P at a first position set on the conveying path of the paper sheet P.

The paper floating detecting unit 147 detects floating-up of a certain level or more of the paper sheet P by using the peripheral surface of the inkjet recording drum 142, which is a suction holding surface of the paper sheet P, as a reference. Therefore, not only the floating-up of the entire paper sheet due to insufficient suction but also partial floating-up due to wrinkles, folding, and the like are detected as floating.

Figure 4:
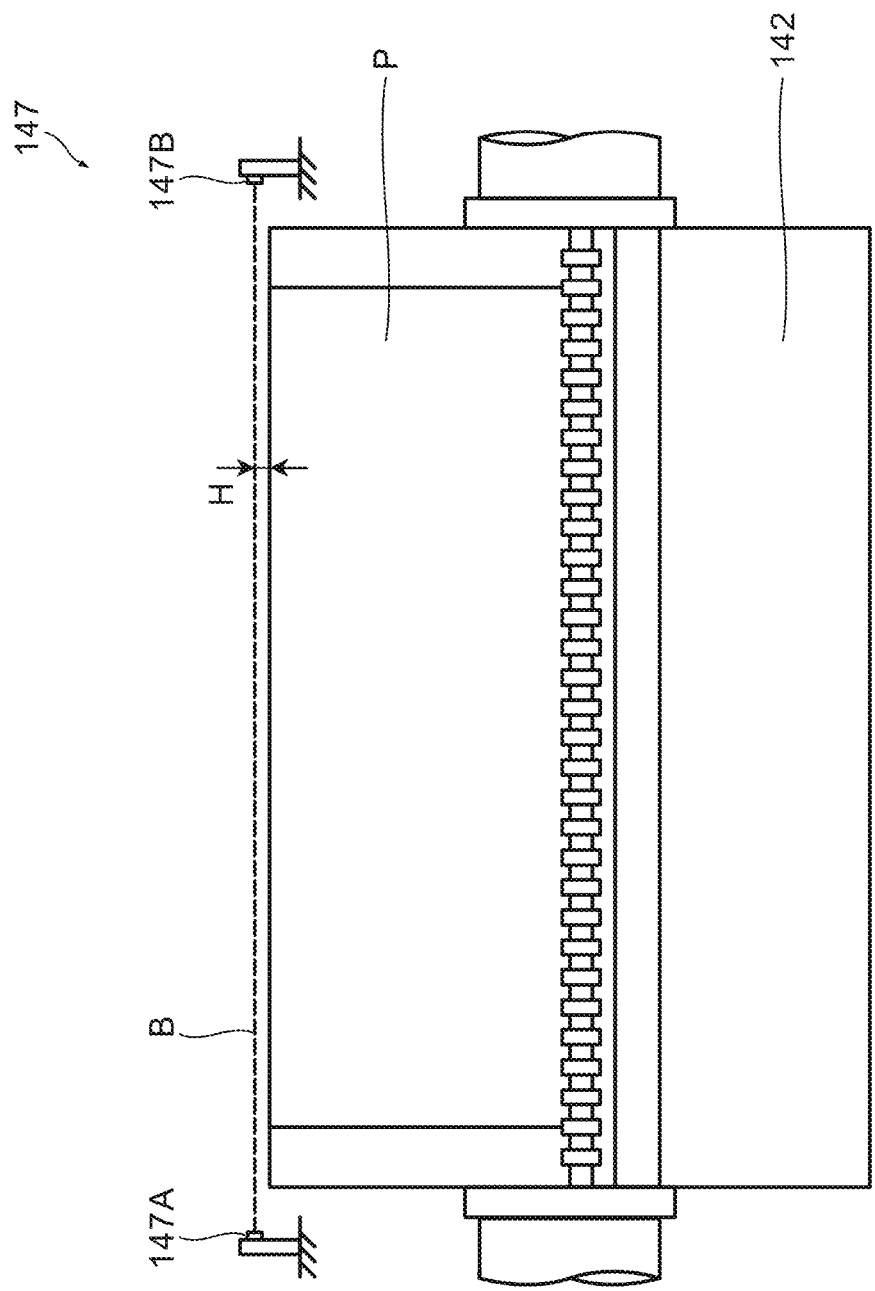
FIG. 4 is a schematic configuration view of a paper sheet floating detecting unit.

FIG. 4 is a schematic configuration view of the paper sheet floating detecting unit. As illustrated in FIG. 4, the paper floating detecting unit 147 includes a projector 147A which emits a detection beam B, and a photo detector 147B which receives the detection beam B emitted from the projector 147A. The projector 147A and the photo detector 147B are arranged facing each other across the inkjet recording drum 142.

For example, the projector 147A emits a laser beam as the detection beam B. The detection beam B is emitted in parallel with the rotating shaft of the inkjet recording drum 142 so as to pass the position at a height H from the peripheral surface of the inkjet recording drum 142. The position at the height H where the detection beam B passes is at the height of detecting the floating of the paper sheet P. The height H is set corresponding to the slow distance and the like.

The photo detector 147B is arranged facing the projector 147A, and receives the detection beam B emitted from the projector 147A.

The configuration of the paper floating detecting unit 147 is as described above. The floating of the paper sheet P is detected as follows.

As described in the foregoing, the detection beam B is set to pass the position at the fixed height H from the peripheral surface of the inkjet recording drum 142. When there is no floating in the paper sheet P, the detection beam B is received by the photo detector 147B without any obstacle.

On the contrary, when the floating is generated in the paper sheet P at the height H or more from the peripheral surface of the inkjet recording drum 142, the detection beam B is blocked by the portion where the floating is generated. As a result, a light receiving amount of the detection beam B received by the photo detector 147B decreases.

Thus, when the floating of a certain level or more is generated, the light receiving amount of the detection beam B in the photo detector 147B decreases. As a result, the floating of the paper sheet P is detectable from the light receiving amount of the detection beam B in the photo detector 147B. Specifically, the floating of the paper sheet P is detected by detecting the light receiving amount equal to or less than the threshold in the photo detector 147B.

The floating of the paper sheet P needs to be detected before the paper sheet P is carried into the ink jet recording unit 145. Therefore, the first position is set on the upstream side of the second position, the first position being the position where the paper floating detecting unit 147 detects the floating of the paper sheet P, the second position being the position where the ink jet recording unit 145 records an image on the paper sheet P. A positional relationship between the first position and the second position is fixed.

—Image Reader—

The image reader 149 is one example of the image reading device. At a third position set on the conveying path of the paper sheet P, an image in the paper sheet P is read line by line. As illustrated in FIG. 2, the image reader 149 includes a line sensor 149A, an image forming lens 149B, and a lighting unit 149C. The line sensor 149A reads an image recorded on the paper sheet P line by line. The line sensor 149A is configured with a one-dimensional charged coupled device (CCD) image sensor or a one-dimensional complementary metal oxide semiconductor (CMOS) image sensor, for example. The image forming lens 149B reduces an optical image on the reading surface of the paper sheet P and forms the image on the light receiving surface of the line sensor 149A. The lighting unit 149C irradiates a region read by the line sensor 149A with illumination light.

Since the image reader 149 needs to read the paper sheet P after an image is recorded thereon, the third position is set on the downstream side of the second position, the third position being the position where the image reader 149 reads the image from the paper sheet P, the second position being the position where the ink jet recording unit 145 records the image on the paper sheet P. A positional relationship between the second position and the third position is fixed. Since the positional relationship between the first position and the second position is fixed as described before, the positional relationship between the first position and the third position is also fixed.

The configuration of the inkjet recording unit 140 is as described above. In the process of conveying the paper sheet P by the inkjet recording drum 142, ink droplets of the respective colors including C, M, Y, and K are deposited on the recording surface of the paper sheet P from the respective inkjet heads 146C, 146M, 146Y, and 146K, which constitute the ink jet recording unit 145, to record a color image on the recording surface.

When floating of a certain level or more is generated in the conveyed paper sheet P in the inkjet recording unit 140, the floating is detected by the paper floating detecting unit 147. When the floating of the paper sheet P is detected by the paper floating detecting unit 147, the processing of retreating the respective inkjet heads 146C, 146M, 146Y, and 146K is immediately performed. This processing is described later in detail.

<Ink Drying Unit>

The ink drying unit 150 performs the dry processing of the recorded paper sheet P. As illustrated in FIG. 1, the ink drying unit 150 includes a chain gripper 152 which conveys the paper sheet P, a sheet guide 154 which guides running of the paper sheet P conveyed by the chain gripper 152, and a heat dryer 156 which heats and thereby dries the recording surface of the paper sheet P conveyed by the chain gripper 152.

The chain gripper 152 receives the paper sheet P from the inkjet recording drum 142, and transports it to the stacking unit 160. The chain gripper 152, which includes an endless chain 152A running along a fixed running path, conveys the paper sheet P by gripping the tip of the paper sheet P by a gripper 152B included in the chain 152A. While being conveyed by the chain gripper 152, the paper sheet P passes through a heating region and a non-heating region set in the ink drying unit 150, and is transported to the stacking unit 160. The heating region is set as the region where the paper sheet P transported from the inkjet recording unit 140 is first conveyed in a horizontal direction. The non-heating region is set as the region where the paper sheet P is conveyed in an inclined direction.

The sheet guide 154 guides conveyance of the paper sheet P conveyed in the heating region and the non-heating region. The sheet guide 154 includes a first guideboard 154A which guides conveyance of the paper sheet P in the heating region, and a second guideboard 154B which guides conveyance of the paper sheet P in the non-heating region. The first guideboard 154A and the second guideboard 154B each have a guide surface to cause the paper sheet P to slide thereon so as to guide conveyance of the paper sheet P. In this case, the first guideboard 154A and the second guideboard 154B suck the paper sheet P. As a consequence, tension can be applied to the paper sheet P to be conveyed. Negative pressure is utilized for suction. The first guideboard 154A and the second guideboard 154B include a number of suction holes on their guide surfaces to suck the paper sheet P through the suction holes to put the paper sheet P in close contact with the guide surfaces.

The heat dryer 156, which is placed in the heating region, heats the paper sheet P conveyed through the heating region to dry the ink applied to the paper sheet P. The heat dryer 156, which includes a plurality of infrared lamps 156A as a heat source, is arranged inside the chain gripper 152. The infrared lamps 156A are arranged at a regular interval along the conveying path of the paper sheet P in the heating region.

The configuration of the ink drying unit 150 is as described above. The paper sheet P is heated and dry-processed by the heat dryer 156 in the process of being conveyed by the chain gripper 152.

<Stacking Unit>

The stacking unit 160 stacks the paper sheets P. As illustrated in FIG. 1, the stacking unit 160 includes a stacking device 162. The stacking device 162 receives the paper sheets P from the chain gripper 152, and stacks them in bundle.

<<Control System>>

Figure 5:
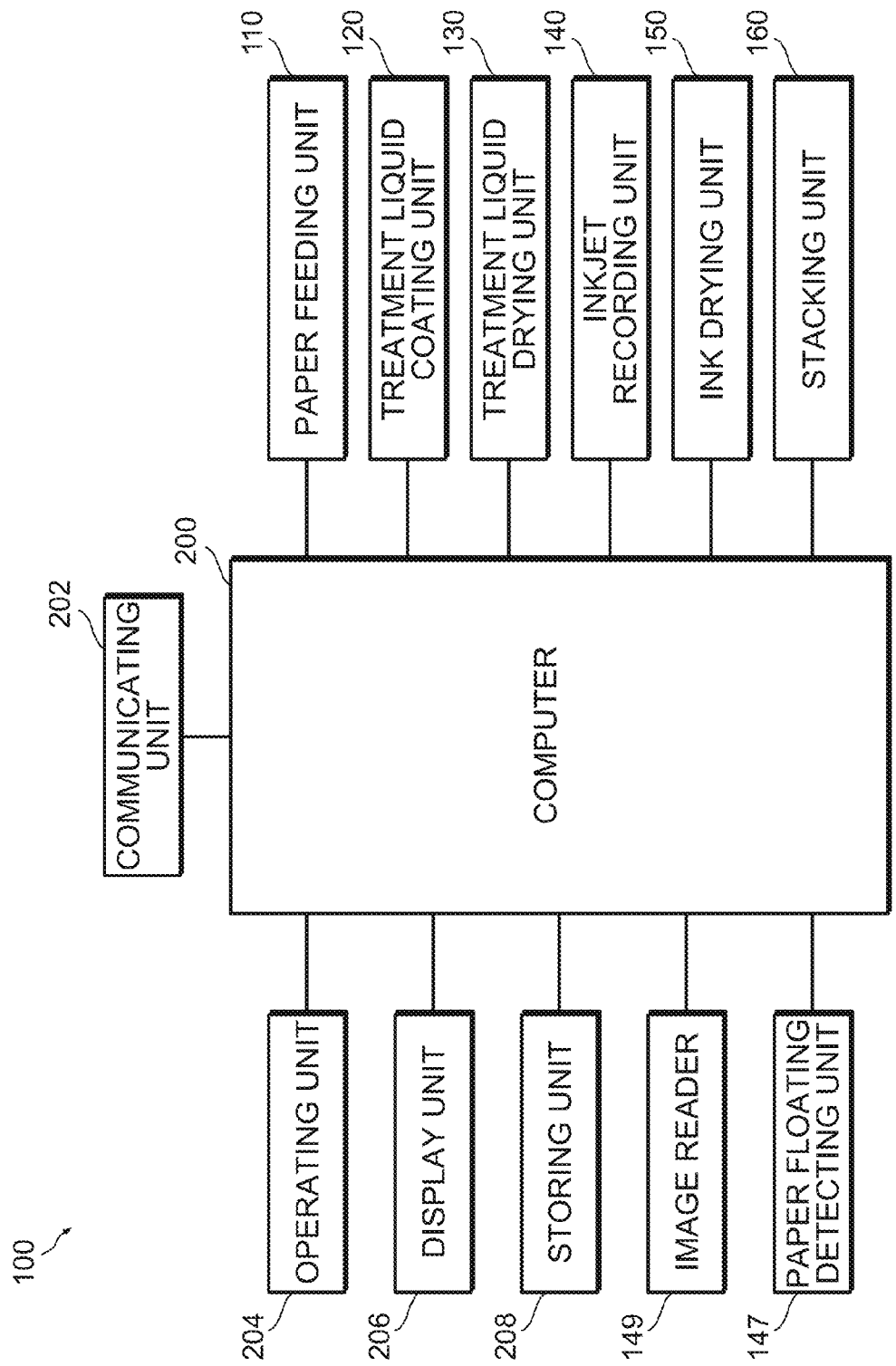
FIG. 5 is a block diagram illustrating a system configuration of a control system of the inkjet recording apparatus.

FIG. 5 is a block diagram illustrating a system configuration of a control system of the inkjet recording apparatus.

As illustrated in FIG. 5, in the inkjet recording apparatus 100, a computer 200 controls operation of each unit. That is, all processing is executed under the control of the computer 200, the processing including paper feeding from the paper feeding unit 110, conveying fed paper sheets P, coating the paper sheets P with treatment liquid in the treatment liquid coating unit 120, drying in the treatment liquid drying unit 130, recording in the inkjet recording unit 140, reading recorded images, drying in the ink drying unit 150, and stacking in the stacking unit 160. The computer 200 functions as a control device of the inkjet recording apparatus 100 by executing specified programs.

The computer 200 is connected to a communicating unit 202, an operating unit 204, a display unit 206, and a storing unit 208.

The communicating unit 202, which includes a communicating device, performs data exchange with external devices in accordance with a prescribed telecommunications standard under the control of the computer 200.

The operating unit 204 includes various operating devices for operating the inkjet recording apparatus 100, and inputs information corresponding to operation of the operating devices into the computer 200.

The display unit 206 includes a display device 170. The display device 170 is one example of the display device. For example, the display device 170 is configured with a color liquid crystal display.

The storing unit 208 includes a storing device. The storing device is configured with a hard disk drive, for example. The storing unit 208 stores a variety of information necessary for control, in addition to the various programs executed by the computer 200.

Figure 6:
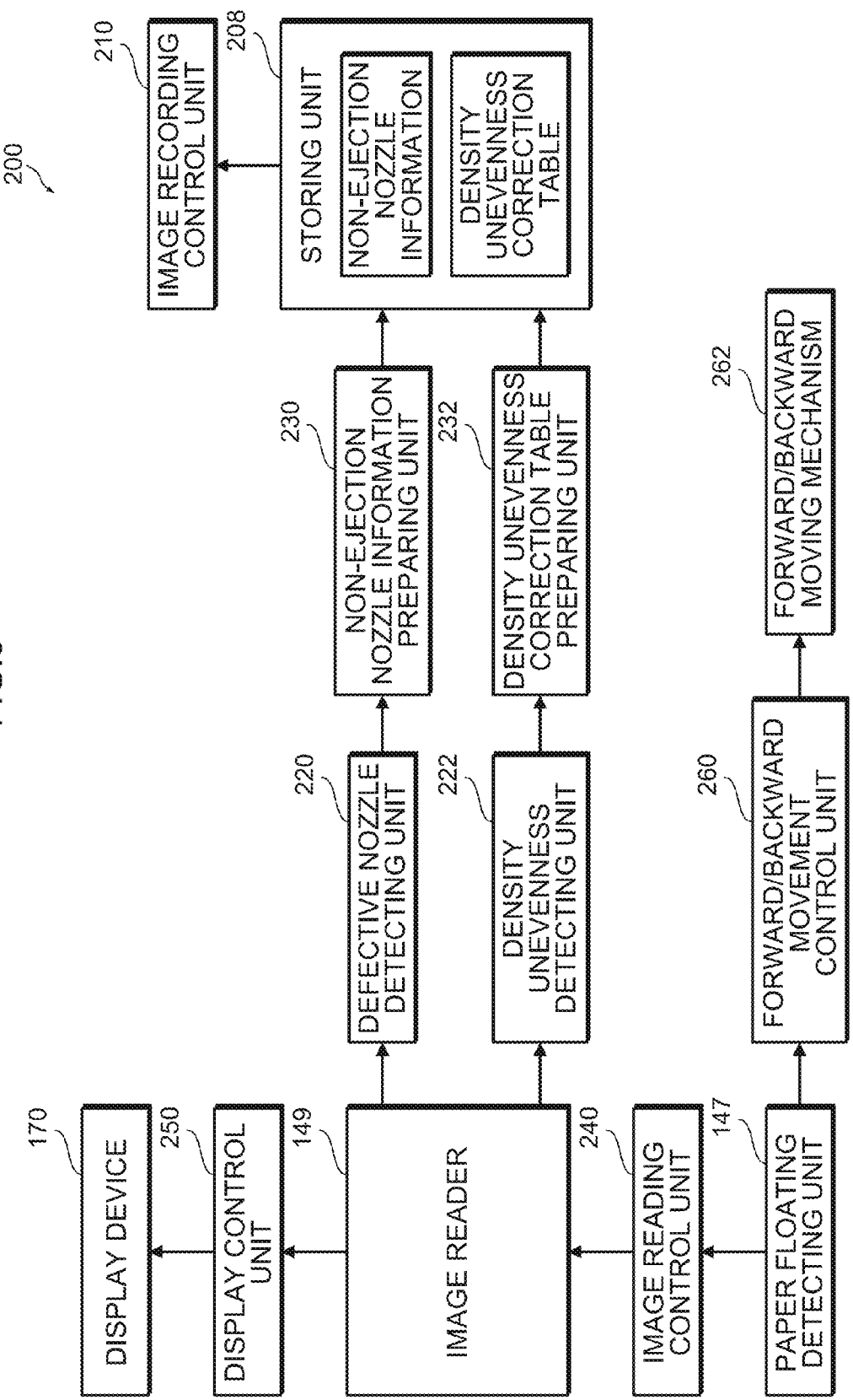
FIG. 6 is a block diagram of the functions implemented when a computer executes specified programs.

FIG. 6 illustrates functional blocks implemented when the computer executes specified programs.

As illustrated in FIG. 6, the computer 200 executes specified programs to function as an image recording control unit 210, a defective nozzle detecting unit 220, a density unevenness detecting unit 222, a non-ejection nozzle information preparing unit 230, a density unevenness correction table preparing unit 232, an image reading control unit 240, a display control unit 250, and a forward/backward movement control unit 260.

<Image Recording Control Unit>

The image recording control unit 210 performs processing of applying various signal processing to image data to generate dot arrangement data, processing of generating driving signals of the inkjet heads based on the generated dot arrangement data, and processing of supplying the generated driving signals to head drivers 212C, 212M, 212Y, and 212K.

Figure 7:
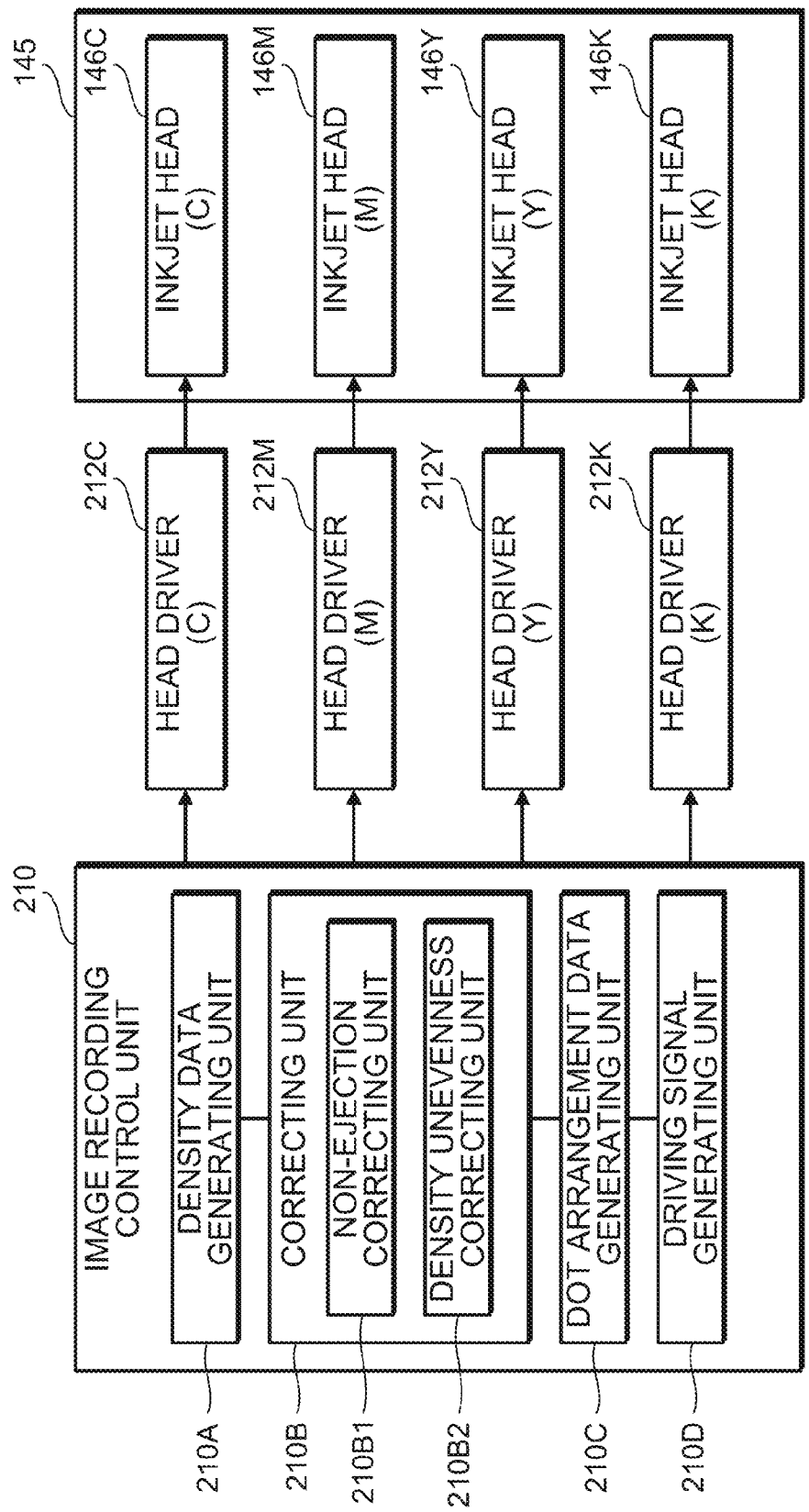
FIG. 7 is a block diagram of an image recording control unit.

FIG. 7 is a block diagram of the image recording control unit.

The image recording control unit 210 includes a density data generating unit 210A, a correcting unit 210B, a dot arrangement data generating unit 210C, and a driving signal generating unit 210D.

The density data generating unit 210A applies density conversion processing to the image data to generate initial density data for each ink color.

The correcting unit 210B includes a non-ejection correcting unit 210B1 and a density unevenness correcting unit 210B2 to perform non-ejection correction and density unevenness correction of the density data generated by the density data generating unit 210A.

The non-ejection correcting unit 210B1 performs non-ejection correction of the density data by using non-ejection nozzle information. The non-ejection nozzle information is the information on the position of an ejection-disabled nozzle. The non-ejection nozzle information is stored in the storing unit 208. As described later, the non-ejection nozzle information is prepared in the non-ejection nozzle information preparing unit 230.

The density unevenness correcting unit 210B2 performs density unevenness correction of density data by using a density unevenness correction table. The density unevenness correction table is stored in the storing unit 208. As described later, the density unevenness correction table is prepared by the density unevenness correction table preparing unit 232.

The dot arrangement data generating unit 210C applies half-toning processing to the corrected density data generated by the correcting unit 210B to generate dot arrangement data.

The driving signal generating unit 210D generates driving signals of the respective inkjet heads 146C, 146M, 146Y, and 146K based on the dot arrangement data generated by the dot arrangement data generating unit 210C.

The driving signals of the respective inkjet heads 146C, 146M, 146Y, and 146K generated by the driving signal generating unit 210D are added to the head drivers 212C, 212M, 212Y, and 212K of the inkjet heads 146C, 146M, 146Y, and 146K, respectively. The head drivers 212C, 212M, 212Y, and 212K drive the inkjet heads 146C, 146M, 146Y, and 146K based on the input driving signals to eject ink from the nozzles.

When the paper floating detecting unit 147 detects floating of the paper sheet P, the image recording control unit 210 acquires the information thereof and stops recording of an image performed by the ink jet recording unit 145. That is, ejection of the ink from the respective inkjet heads 146C, 146M, 146Y, and 146K is stopped. This means that the image recording control unit 210 also has a function as the image recording stop control unit.

<Defective Nozzle Detecting Unit>

The defective nozzle detecting unit 220 detects a defective nozzle from the inkjet heads. The defective nozzle refers to a non-ejection nozzle and an inclined-ejection nozzle. The non-ejection nozzle refers to a nozzle ejection-disabled due to clogging, failure, and the like. The inclined-ejection nozzle refers to a nozzle having impact position errors, the amount of which is equal to or more than a specified amount.

Detection of the defective nozzle is performed based on the result of recording a specified test chart. The result of recording is read by the image reader 149. The defective nozzle detecting unit 220 analyzes image data of the test chart read by the image reader 149, and detects a defective nozzle.

Figure 8:
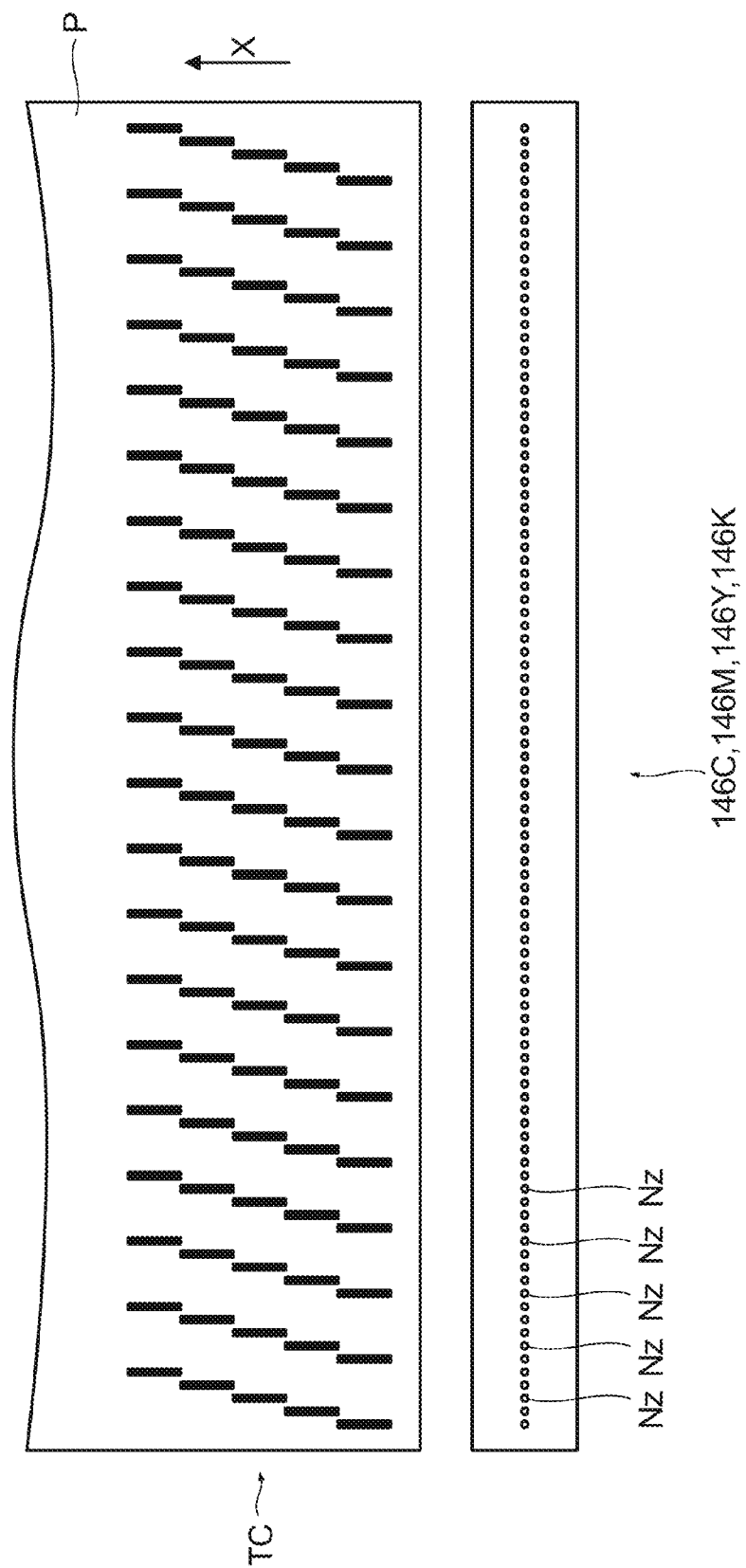
FIG. 8 illustrates one example of a test chart for defective nozzle detection.

FIG. 8 illustrates one example of the test chart for defective nozzle detection.

The test chart TC illustrated in FIG. 8 is a test chart called a nozzle check pattern. The nozzle check pattern is recorded by depositing ink droplets stepwise from the respective nozzles.

Figure 9:
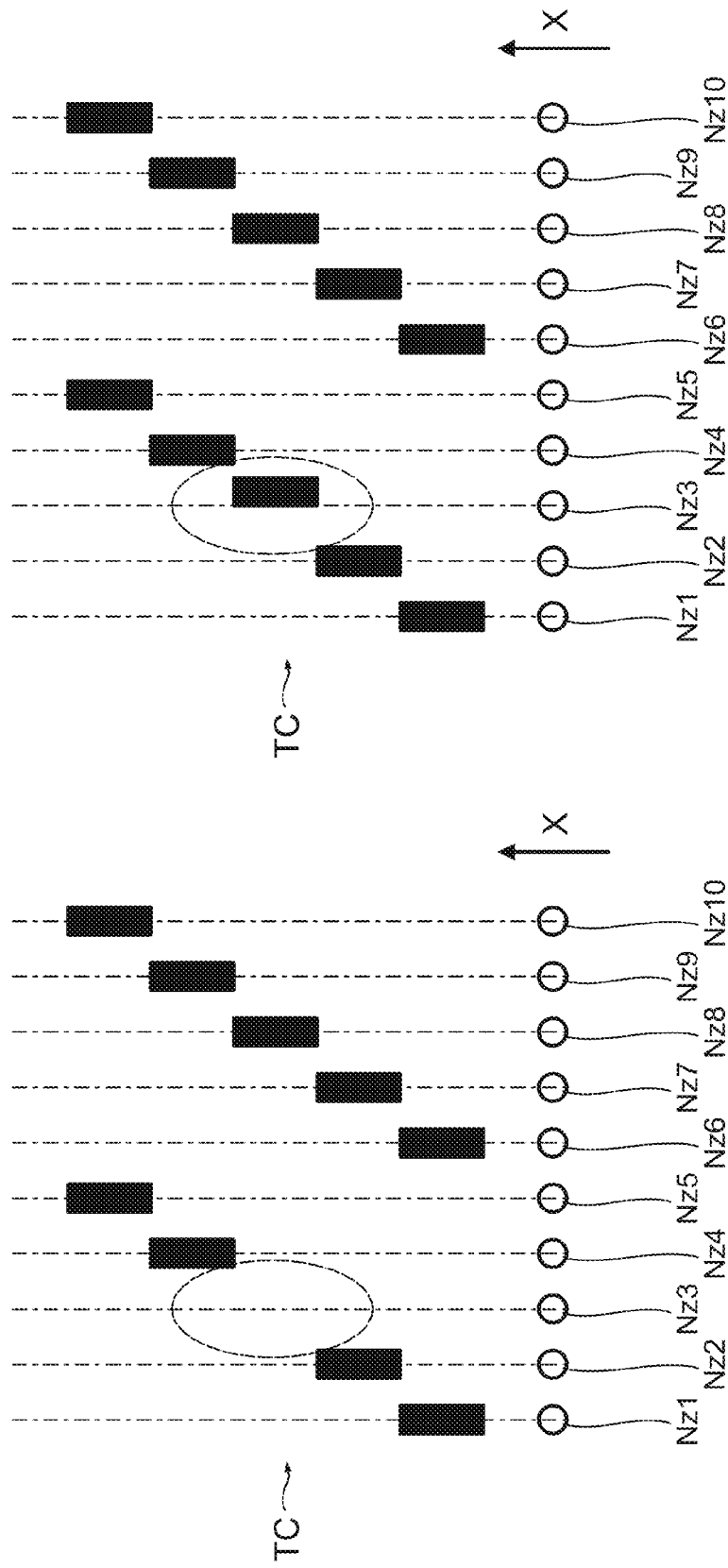
FIGS. 9A and 9B are concept views in the case of detecting a defective nozzle using a nozzle check pattern.

FIGS. 9A and 9B are concept views in the case of detecting a defective nozzle using the nozzle check pattern. FIG. 9A is a concept view in the case of detecting a non-ejection nozzle. FIG. 9B is a concept view in the case of detecting an inclined-ejection nozzle.

FIG. 9A illustrates the case where a third nozzle Nz3 from the left is in a non-ejection state. As illustrated in FIG. 9A, when any nozzle is in the non-ejection state when the nozzle check pattern is used, the pattern to be formed by the nozzle in the non-ejection state is missing. Therefore, by detecting the position of the missing pattern, the non-ejection nozzle can be detected and the position thereof can be identified.

FIG. 9B illustrates the case where inclined ejection occurs in a third nozzle Nz3 from the left. As illustrated in FIG. 9B, when inclined ejection occurs in the case where the nozzle check pattern is used, the recorded pattern of the nozzle having inclined ejection deviates from its regular position. Here, the regular position is the position of the pattern recorded when the ejection direction is not inclined. Therefore, by detecting the recorded pattern deviating from the regular position, the inclined-ejection nozzle can be detected and the position thereof can be identified.

Figure 10:
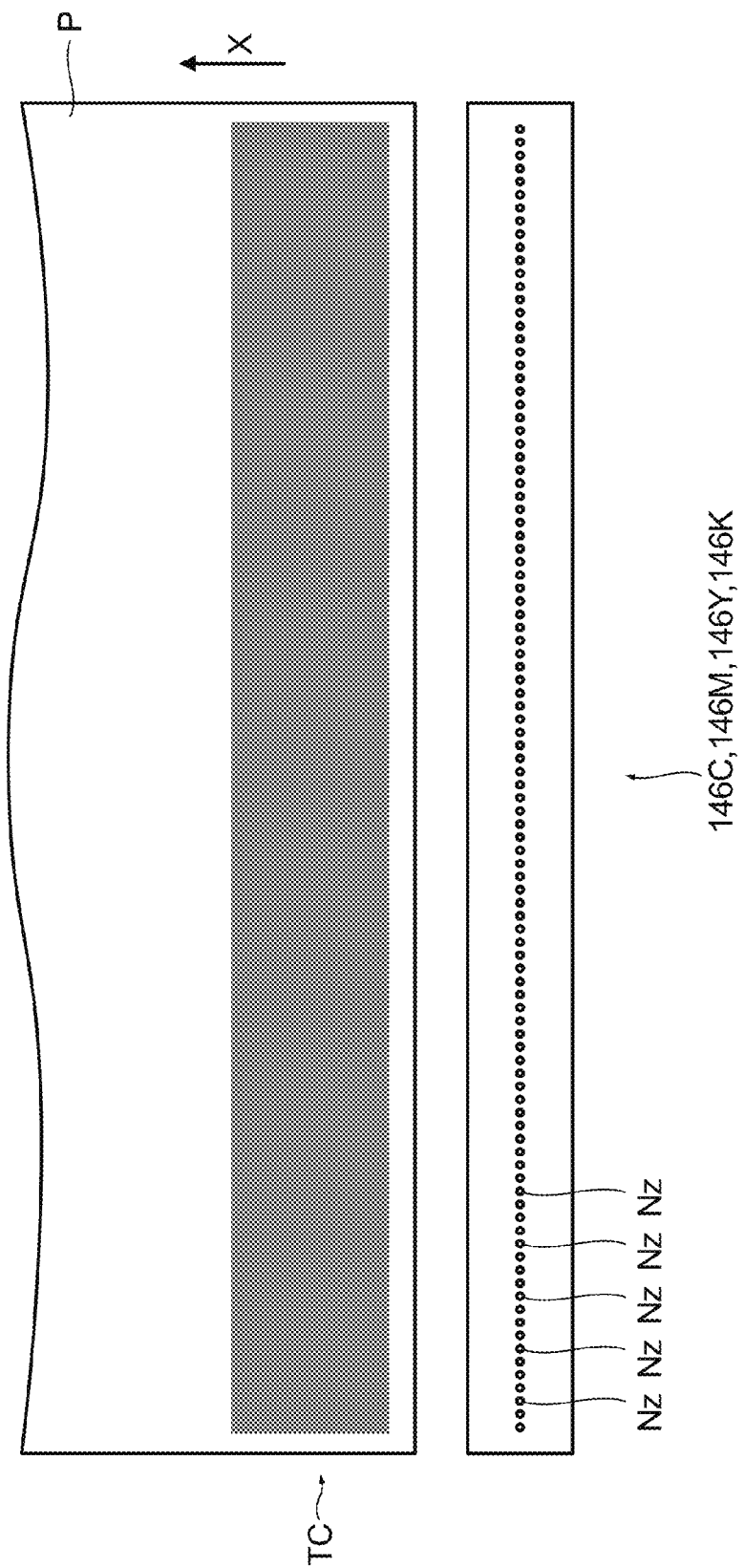
FIG. 10 illustrates another example of the test chart for defective nozzle detection.

FIG. 10 illustrates another example of the test chart for defective nozzle detection.

The test chart TC illustrated in FIG. 10 is a test chart called an isoconcentration patch. The isoconcentration patch is a test chart recorded at a uniform density in the entire crosswise region.

Figure 11:
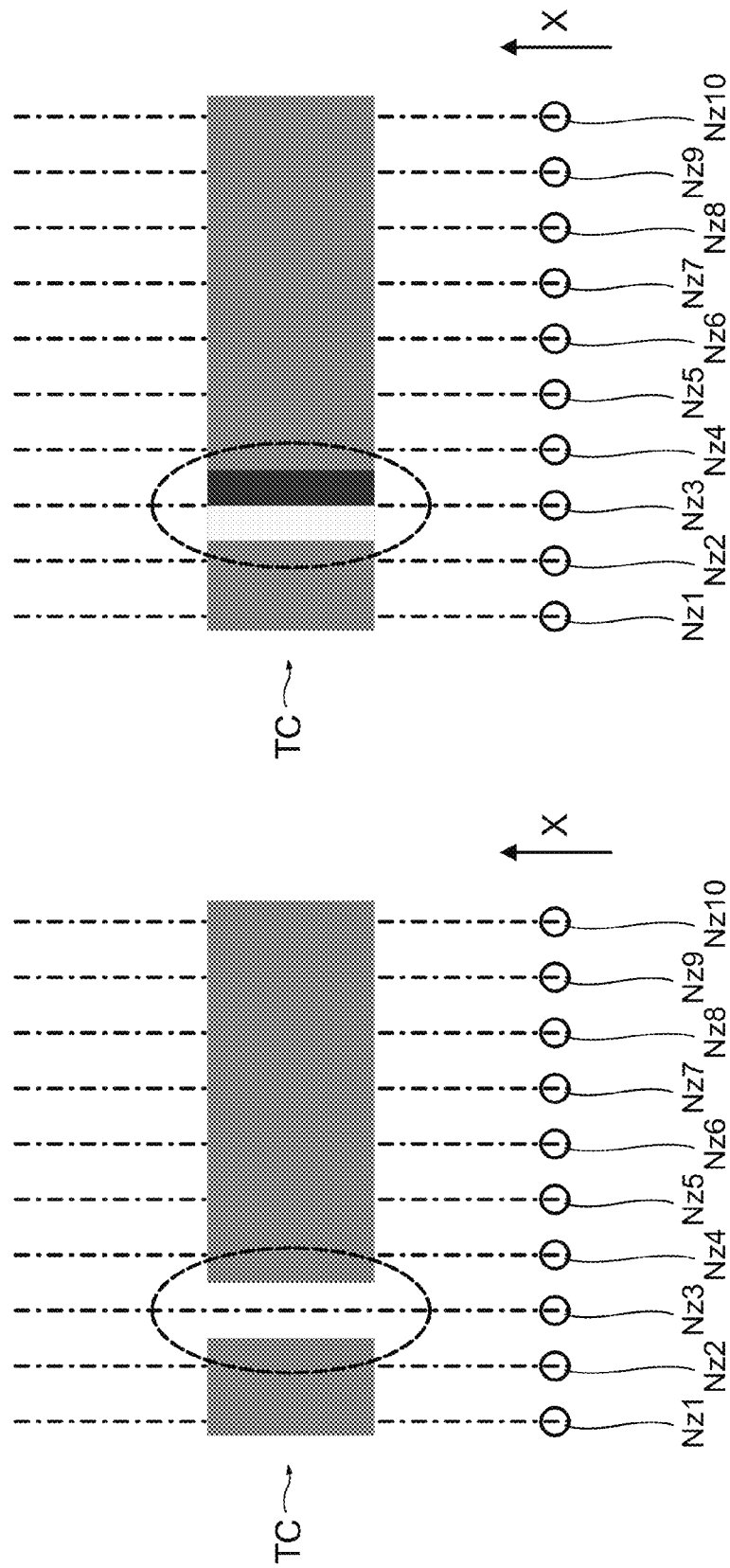
FIGS. 11A and 11B are concept views in the case of detecting defective nozzles using an isoconcentration patch.

FIGS. 11A and 11B are concept views in the case of detecting defective nozzles using the isoconcentration patch. FIG. 11A is a concept view in the case of detecting a non-ejection nozzle. FIG. 11B is a concept view in the case of detecting an inclined-ejection nozzle.

FIG. 11A illustrates the case where a third nozzle Nz3 from the left is in the non-ejection state. As illustrated in FIG. 11A, when a nozzle is in the non-ejection state when the isoconcentration patch is used, a portion corresponding to the nozzle in the non-ejection state is missing in the recorded chart. Therefore, by detecting the missing portion in the recorded test chart, the non-ejection nozzle can be detected and the position thereof can be identified.

FIG. 11B illustrates the case where inclined ejection occurs in a third nozzle Nz3 from the left. As illustrated in FIG. 11B, when inclined ejection occurs when the isoconcentration patch is used, the density in the vicinity of the nozzle causing inclined ejection changes. Therefore, by detecting a density change portion in the recorded test chart, the inclined-ejection nozzle can be detected and the position thereof can be identified.

When the specified test chart TC is recorded in this way, a defective nozzle can be detected and the position thereof can be identified.

Defective nozzle detection is performed for each inkjet head. Since the inkjet recording apparatus 100 of the present embodiment includes four inkjet heads, defective nozzle detection is performed in each of these inkjet heads.

Defective nozzle detection is constantly carried out during recording. That is, whenever image recording is performed on one paper sheet P, the defective nozzle detection is performed. The defective nozzle detection during recording is carried out by recording the test chart TC for defective nozzle detection in a margin region of the paper sheet P.

Figure 12:
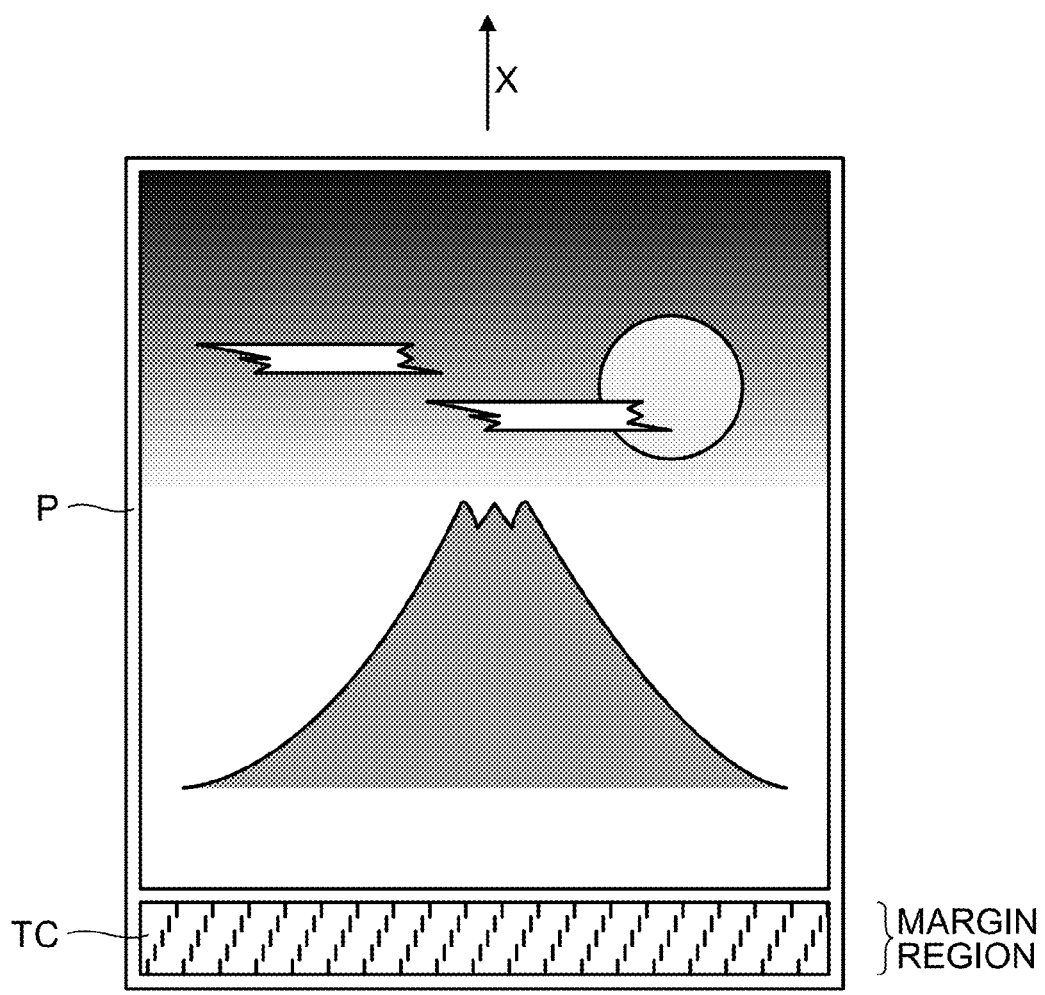
FIG. 12 illustrates an example of recording an image on a paper sheet.

FIG. 12 illustrates an example of recording an image on the paper sheet.

As illustrated in FIG. 12, a recording target image is recorded on the paper sheet P with a margin. The margin is formed in one end of the conveyance direction X of the paper sheet P. The test chart TC is recorded on the margin region. By recording the test chart TC for defective nozzle detection on the margin region of the paper sheet P in this way, defective nozzle detection can be performed whenever an image is recorded on one paper sheet P.

As described in the foregoing, defective nozzle detection is performed for every inkjet head. In this case, the inkjet head to be checked may be switched in each sheet, or all the inkjet heads may be checked in each sheet. When the inkjet head to be checked is switched in each sheet, the inkjet head which records the test chart is switched in a regular cycle to record the test chart on the margin region. When all the inkjet heads are checked, the test chart is recorded on the margin region by all the inkjet heads.

In the case of defective nozzle detection, an image is read only in the region where the test chart TC is recorded. That is, reading is performed only in the margin region.

<Density Unevenness Detecting Unit>

The density unevenness detecting unit 222 detects the density unevenness of an image recorded by the inkjet heads. Density unevenness detection is performed based on the result of recording a specified test chart. The result of recording is read by the image reader 149. The density unevenness detecting unit 222 analyzes image data of the test chart read by the image reader 149, and detects density unevenness.

Figure 13:
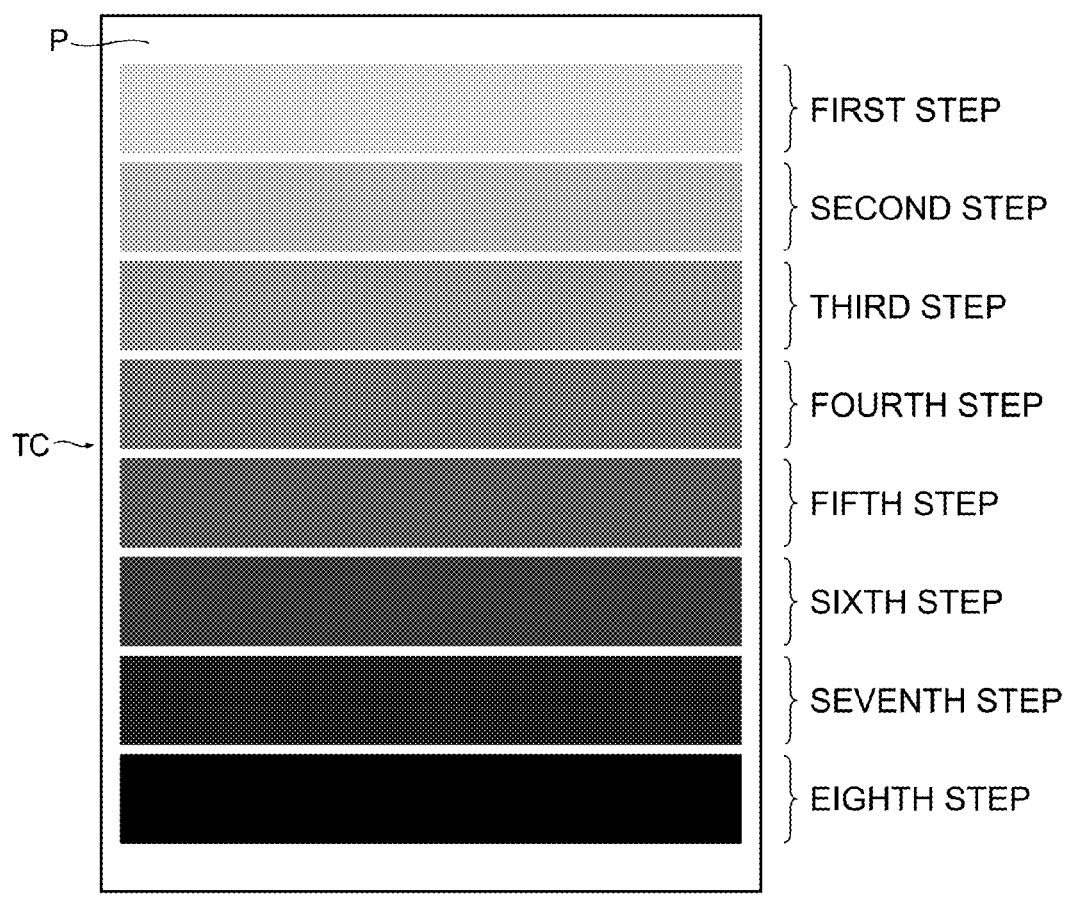
FIG. 13 illustrates one example of a test chart for detecting density unevenness.
Figure 14:
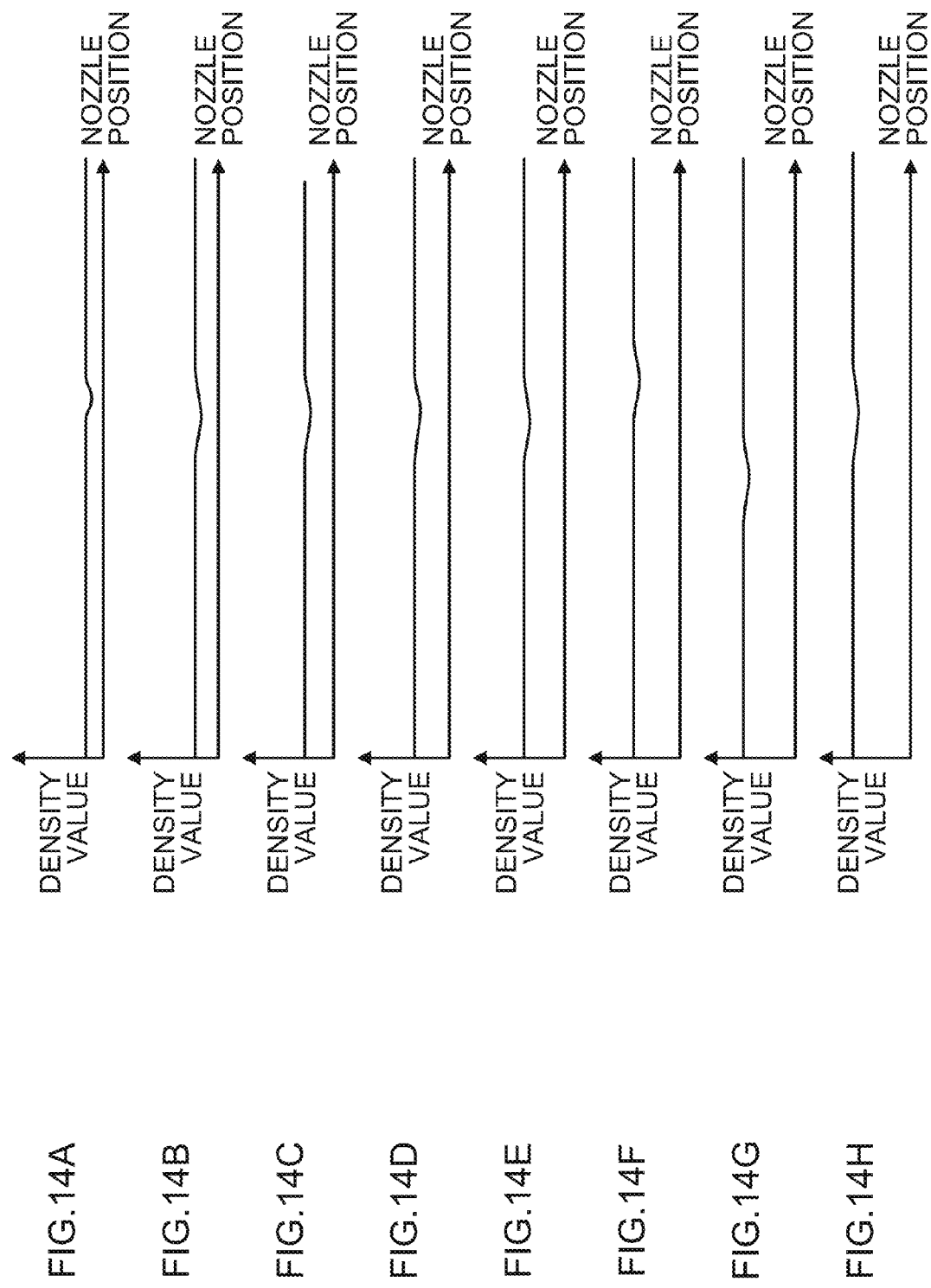
FIGS. 14A to 14H are graph views illustrating examples of gradation density values read from the density chart, respectively.

FIG. 13 illustrates one example of a test chart for detecting density unevenness.

The test chart TC illustrated in FIG. 13 is a test chart called a density chart. The density chart is a chart in which the density is arrayed stepwise. In the example illustrated in FIG. 13, an example of the density chart of eight steps is indicated. In the density chart of eight steps, the density from lowest density to highest density is expressed as gradation of eight steps. A first step of the chart corresponds to a portion of the lowest density, and an eighth step corresponds to a portion of the highest density.

The density unevenness detecting unit 222 detects a density value of each gradation level in the density chart, and detects density unevenness in each gradation level.

FIGS. 14A to 14H are graph views illustrating examples of gradation density values read from the density chart, respectively. In FIGS. 14A to 14H, a vertical axis represents a density value and a horizontal axis represents a nozzle position in the width direction. FIGS. 14A to 14H illustrate the results of detecting density values in the first step to the eighth step in the density chart, respectively. As illustrated in FIGS. 14A to 14H, the density values are detected for the respective gradation levels in the density chart, and density unevenness is detected in each gradation level.

Density unevenness detection is performed for each inkjet head. Since the inkjet recording apparatus 100 of the present embodiment includes four inkjet heads, detection of density unevenness is performed in each of these inkjet heads. In this case, the test chart of one inkjet head is recorded on one paper sheet, or the test charts of all the inkjet heads may be recorded on one paper sheet.

Density unevenness detection is carried out in each job. The job refers to an image recording command issued to the inkjet recording apparatus. In addition, density unevenness detection is also carried out at the timing instructed by a user, after startup of the apparatus, after execution of maintenance operation, and the like.

In the case of detecting the density unevenness, an image is read only in the region where the test chart TC is recorded. When the test chart for density unevenness detection is recorded on one paper sheet as illustrated in FIG. 13, the image is read from the entire paper sheet.

<Non-Ejection Nozzle Information Preparing Unit>

The non-ejection nozzle information preparing unit 230 prepares non-ejection nozzle information based on the result of defective nozzle detection carried out in the defective nozzle detecting unit 220. That is, the detected defective nozzle is disabled from ejecting, and information on the position of the nozzle is prepared as the non-ejection nozzle information. The non-ejection nozzle information is prepared for each inkjet head. The prepared non-ejection nozzle information is stored in the storing unit 208.

The non-ejection correcting unit 210B1 performs non-ejection correction by a known method based on the prepared non-ejection nozzle information. For example, non-ejection correction is performed by increasing the amount of ejection from the nozzles around the ejection-disabled nozzle. The processing of increasing the ejection amount is performed by, for example, increasing the number of dots per unit or increasing a droplet amount.

<Density Unevenness Correction Table Preparing Unit>

The density unevenness correction table preparing unit 232 prepares a density unevenness correction table based on the result of density unevenness detection carried out in the density unevenness detecting unit 222. The density unevenness correction table is prepared for each inkjet head. The prepared density unevenness correction table is stored in the storing unit 208.

Figure 15:
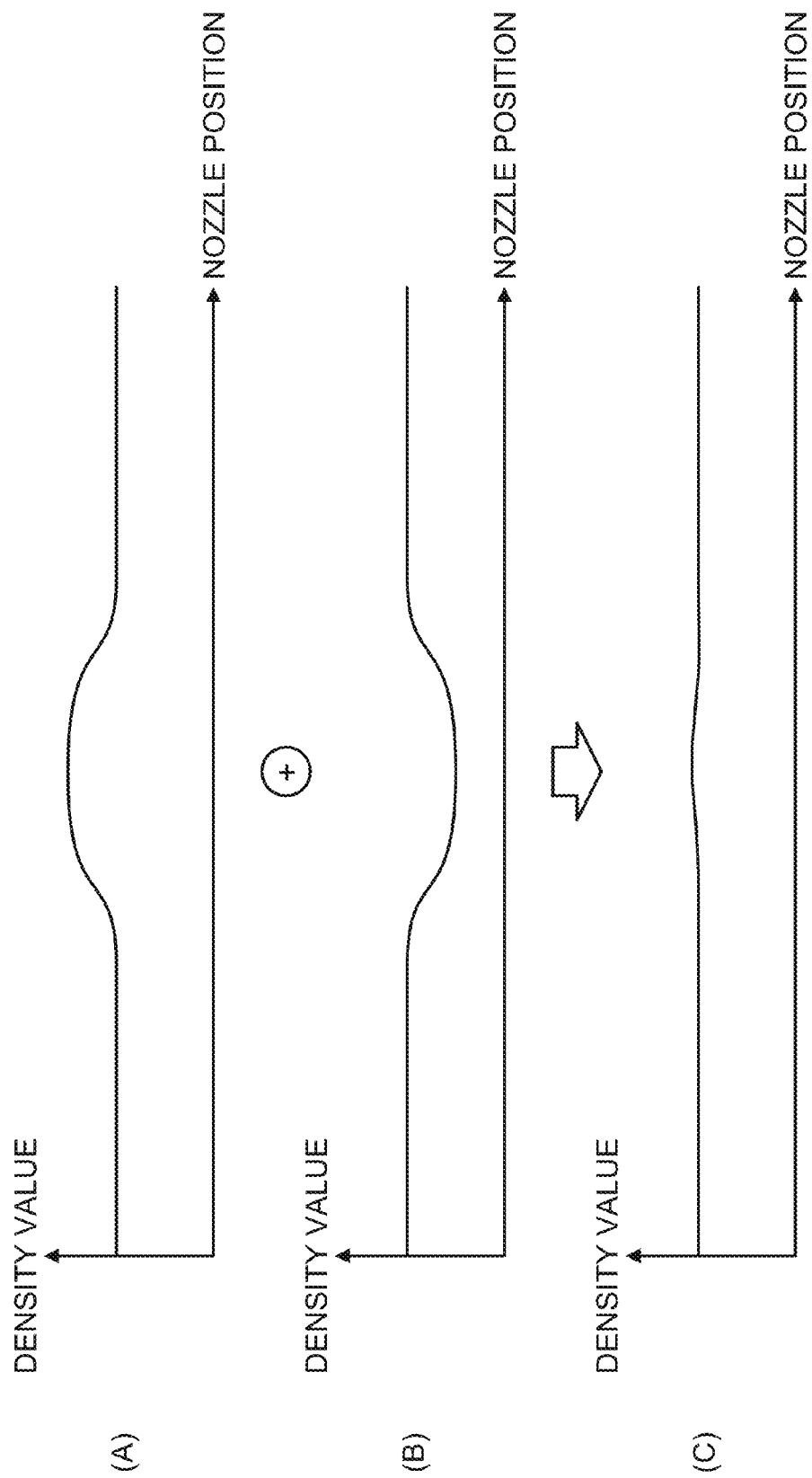
FIG. 15 is a concept view for preparation of a density unevenness correction table and correction of density unevenness.

FIG. 15 is a concept view for preparation of the density unevenness correction table and correction of density unevenness.

Portion (A) of FIG. 15 illustrates one example of the result of detecting density unevenness. Portion (B) of FIG. 15 illustrates one example of the density unevenness correction table prepared from the detection result of the density unevenness illustrated in Portion (A) of FIG. 15. Portion (C) of FIG. 15 is one example of a density value after the density unevenness is corrected using the density unevenness correction table illustrated in Portion (B) of FIG. 15. In each of the drawings, a vertical axis represents a density value and a horizontal axis represents a nozzle position in a longitudinal direction of the inkjet head.

As illustrated in Portion (B) of FIG. 15, the density unevenness correction table preparing unit 232 prepares a density unevenness correction table for all the nozzles to be used so that the density values of the respective gradation levels in the density chart read by the image reader become uniform in the width direction.

The density unevenness correcting unit 210B2 performs density unevenness correction by performing gradation conversion of density data of an image to be recorded by using the prepared density unevenness correction table. This makes it possible to obtain an image in which the density in the width direction is substantially uniform in each gradation level as illustrated in Portion (C) of FIG. 15.

<Image Reading Control Unit>

The image reading control unit 240 controls reading by the image reader 149. As described in the foregoing, defective nozzle detection and density unevenness detection are performed by recording a specified test chart on the paper sheet P, and reading the image of the recorded test chart with the image reader 149. When the defective nozzle and density unevenness are detected, the image reading control unit 240 controls driving of the image reader 149 so that the image of the test chart recorded on the paper sheet P is read with the image reader 149.

Since defective nozzle detection is carried out in each sheet, driving of the image reader 149 is controlled so that reading is performed in each sheet. In this case, reading by the image reader 149 is controlled so that the region where the test chart is recorded is read.

Contrary to this, density unevenness detection is performed in each job. Accordingly, driving of the image reader 149 is controlled so that reading is performed in response to the timing of execution of the density unevenness detection.

Thus, the image reading control unit 240 controls driving of the image reader 149 so that the image of the test chart recorded on the paper sheet P is read with the image reader 149 when the defective nozzle and density unevenness are detected. In addition, when floating of the paper sheet P is detected by the paper floating detecting unit 147, the image reading control unit 240 controls driving of the image reader 149 so that the image of the paper sheet P having floating is read by the image reader 149. Hereinafter, a detailed description is given of the reading control.

—Reading Control When Floating is Detected—

In the inkjet recording apparatus 100 of the present embodiment, when floating of the paper sheet P is detected in the inkjet recording unit 140, the image of the paper sheet P in which the floating is detected is read with the image reader 149. In this case, the image reader 149 reads the image in a fixed front and rear range in the conveyance direction of the paper sheet P with the position where floating is detected as a reference.

Figure 16:
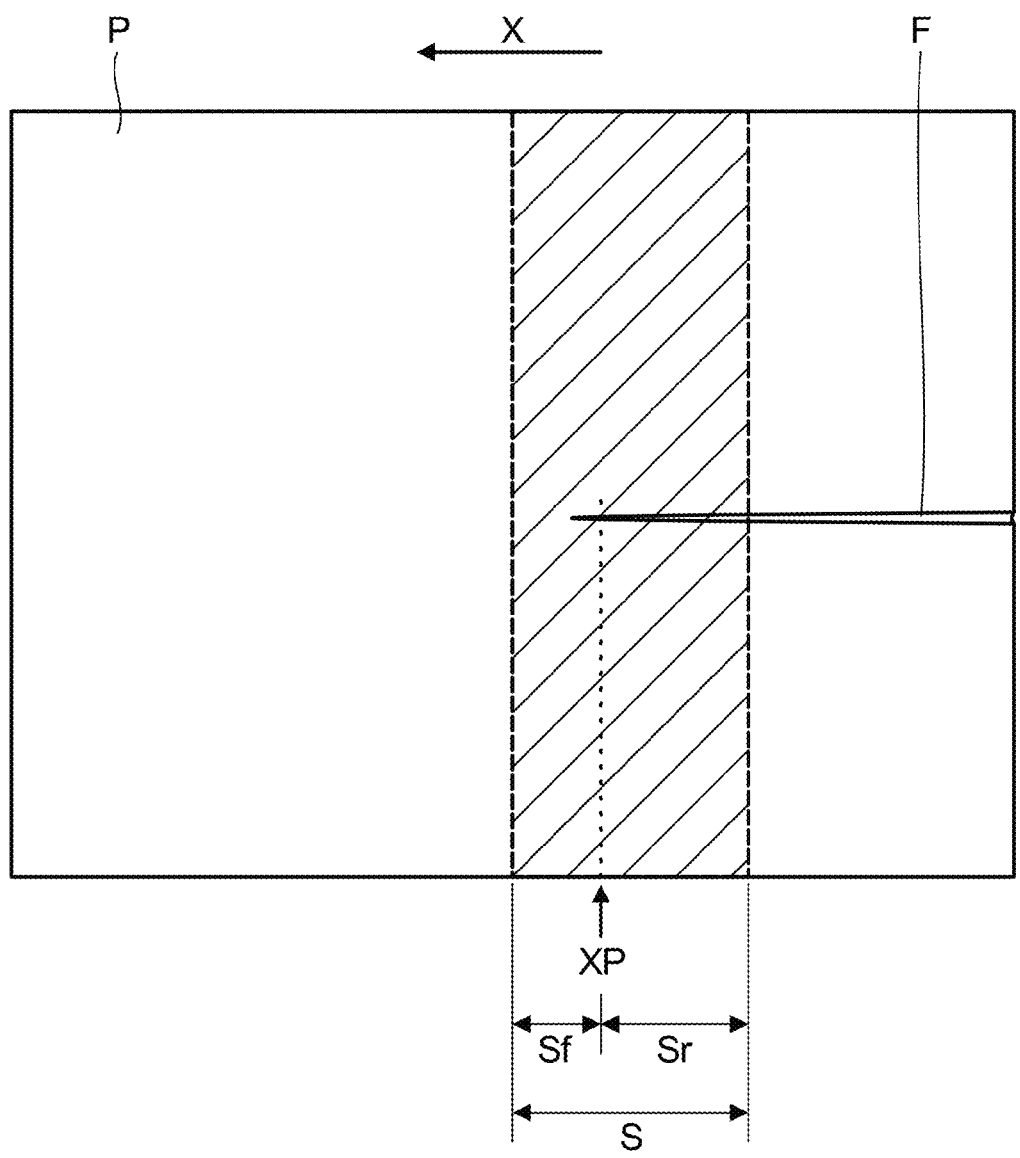
FIG. 16 is a concept view for image reading when floating is detected.

FIG. 16 is a concept view of reading an image when floating is detected.

FIG. 16 illustrates the case where a "longitudinal wrinkle" is generated in the paper sheet P, so that floating F is detected. The longitudinal wrinkle is a stripe-like wrinkle extending along the conveyance direction X of the paper sheet P.

Assume that the floating F generated in the paper sheet P is detected at a position XP. In this case, a fixed front and rear range along the conveyance direction X of the paper sheet P is set as an image reading range S with the position XP where floating F is detected as a reference. Specifically, with the position XP where the floating F is detected as a reference, a front reading range Sf is set in a fixed front range in the conveyance direction X of the paper sheet P and a rear reading range Sr is set in a fixed rear range, by which the entire reading range S is set. In FIG. 16, a region expressed by a slanting line is the image reading range S.

When floating of the paper sheet P is detected by the paper floating detecting unit 147, the image reading control unit 240 controls driving of the image reader 149 so that the image in the fixed front and rear range in the conveyance direction of the paper sheet P is read with the floating detection position XP as a reference. Specifically, when floating is detected, driving of the image reader 149 is controlled so that reading is started after the lapse of prescribed time from the detection, and reading is finished after the lapse of prescribed time from the start of reading. The distance between the position (first position) where the paper floating detecting unit 147 detects floating of the paper sheet P and the position (third position) where the image reader 149 reads an image in the paper sheet P is known, and the conveying speed of the paper sheet P is also known. Accordingly, when reading is started after the lapse of prescribed time from detection of the floating, and reading is finished after the lapse of prescribed time from the start of reading, the image in a desired range can be read. The time to start reading and the time to finish reading are set in accordance with the reading range S and the conveying speed of the paper sheet P.

<Display Control Unit>

The display control unit 250 controls display of an image on the display device 170. Information such as information on an operation condition of the inkjet recording apparatus 100 is displayed on the display device 170.

In the case where floating of the paper sheet P is detected by the paper floating detecting unit 147 in particular, the display control unit 250 carries out following display control. That is, when floating of the paper sheet P is detected by the paper floating detecting unit 147, the display control unit 250 acquires an image read with the image reader 149, and displays the image on the display device 170.

Figure 17:
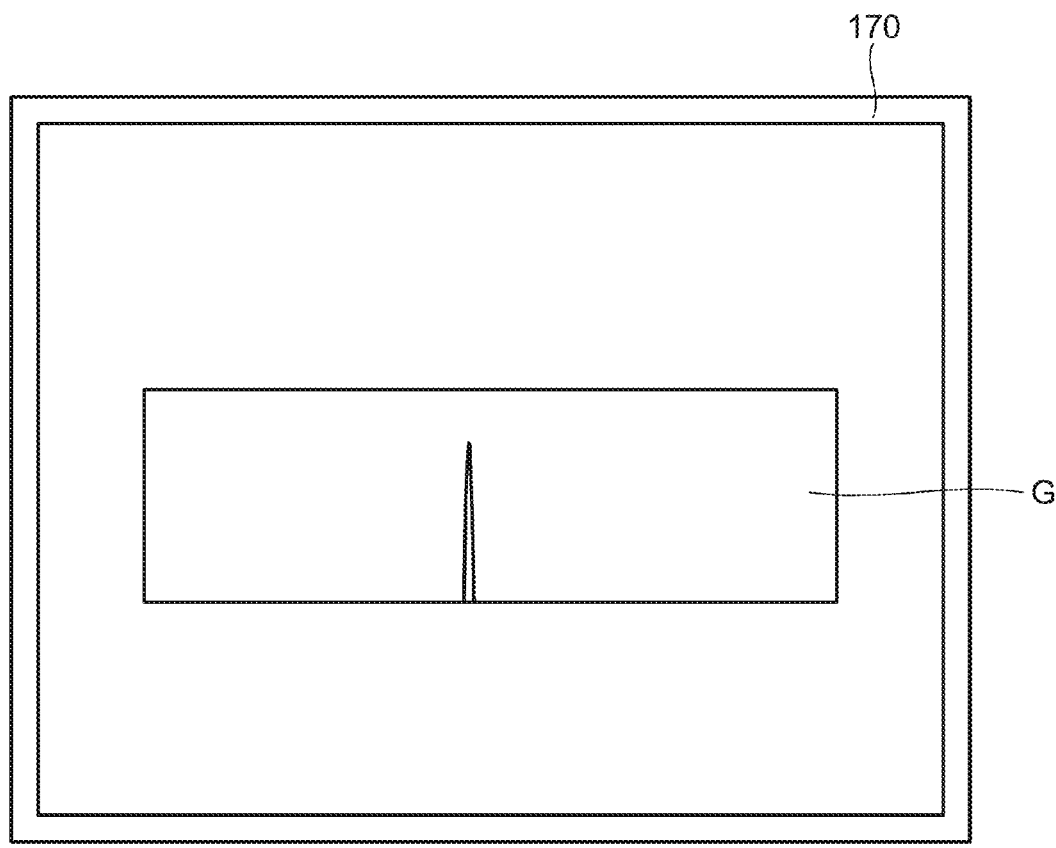
FIG. 17 illustrates an example of a read image displayed on a display device.

FIG. 17 illustrates an example of a read image displayed on the display device. As illustrated in FIG. 17, an image G read with the image reader 149 is displayed on the display device 170. An operator can discriminate the type of the floating generated in the paper sheet P by visually confirming the display of the display device 170.

<Forward/Backward Movement Control Unit>

The forward/backward movement control unit 260 controls a forward/backward moving mechanism 262 provided in the carriage so as to control forward/backward movement of the respective inkjet heads 146C, 146M, 146Y, and 146K. Specifically, the forward/backward movement of the respective inkjet heads 146C, 146M, 146Y, and 146K is controlled so that the preset slow distance is obtained. The forward/backward movement control is performed whenever the thickness of the paper sheet P is changed.

In the case where floating of the paper sheet P is detected by the paper floating detecting unit 147, the forward/backward movement control unit 260 carries out retreating control. More specifically, when floating of the paper sheet P is detected by the paper floating detecting unit 147, the respective inkjet heads 146C, 146M, 146Y, and 146K are simultaneously retreated so that the nozzle faces of the respective inkjet heads 146C, 146M, 146Y, and 146K are moved to the positions at a fixed height from the inkjet recording drum 142, respectively. Accordingly, even when the paper sheet P having floating continues to be conveyed, the paper sheet P can be prevented from contacting the inkjet heads 146C, 146M, 146Y, and 146K.

<<Overall Processing Flow by Inkjet Recording Apparatus>>

In the inkjet recording apparatus 100 of the present embodiment, the paper sheet P is processed in order of (a) paper feeding, (b) coating with treatment liquid, (c) drying of treatment liquid, (d) image recording, (e) ink drying, and (f) stacking.

First, a paper sheet P is fed from the paper feeding unit 110. The paper sheet P fed from the paper feeding unit 110 is conveyed to the treatment liquid coating unit 120. Then, in the process of conveying the paper sheet P by the treatment liquid coating drum 122 of the treatment liquid coating unit 120, a recording surface of the paper sheet P is coated with a treatment liquid.

The paper sheet P coated with the treatment liquid is then conveyed to the treatment liquid drying unit 130. Then, in the process of being conveyed by the treatment liquid drying drum 132 of the treatment liquid drying unit 130, the paper sheet P is dry-processed with warm air blown to the recording surface.

The dry-processed paper sheet P is then conveyed to the inkjet recording unit 140. Then, in the process of conveying the paper sheet P with the inkjet recording drum 142 of the inkjet recording unit 140, ink droplets of respective colors including cyan, magenta, yellow, and black are deposited to record a color image on the paper sheet P.

The paper sheet P with the image recorded thereon is then conveyed to the ink drying unit 150. Then, in the process of conveying the paper sheet P by the chain gripper 152 of the ink drying unit 150, heat from the infrared lamps 156A is applied to the recording surface, so that the paper sheet P is dry-processed.

The dry-processed paper sheet P is then directly conveyed to the stacking unit 160 by the chain gripper 152, and is collected by the stacking device 162 of the stacking unit 160.

<<Processing Procedures of Paper Sheet in Inkjet Recording Unit>>

Figure 18:
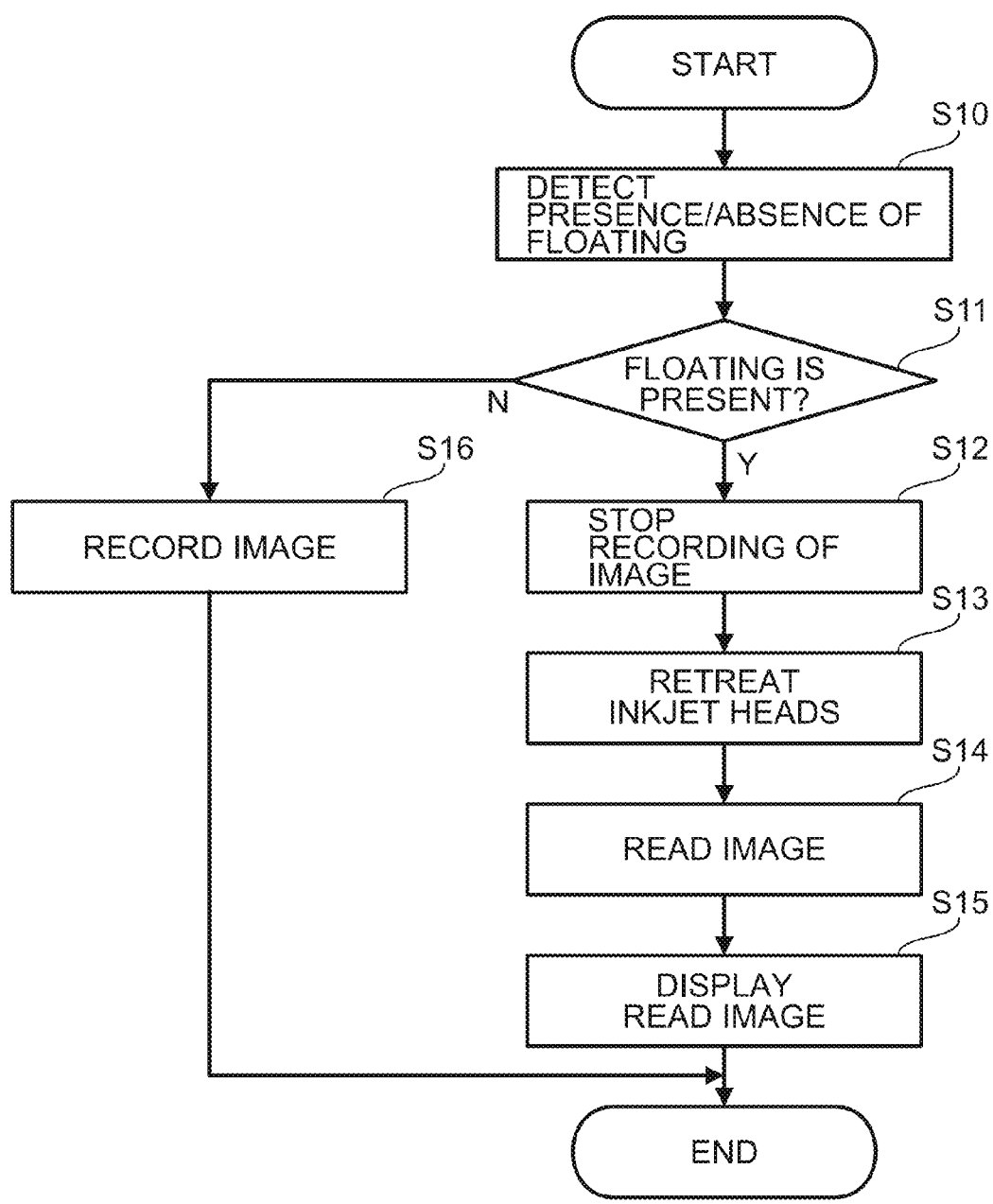
FIG. 18 is a flow chart illustrating processing procedures of a paper sheet in the inkjet recording unit.

FIG. 18 is a flow chart illustrating processing procedures of the paper sheet in the inkjet recording unit.

The paper sheet P received and delivered to the inkjet recording drum 142 is first subjected to detection of the presence/absence of floating in the paper floating detecting unit 147 (step S10). Based on the detection result of the floating, the presence/absence of floating is determined (step S11).

When it is determined that floating is not present as a result of detection of floating, image recording is immediately performed (step S16).

When it is determined that flowing is present, image recording on the paper sheet P is stopped (step S12). However, conveyance of the paper sheet P is continuously performed. When recording has already been started, recording is stopped midway. It is to be noted that recording is stopped only for the paper sheet detected to have floating. Even when floating is detected in one paper sheet while recording is performed on a paper sheet preceding thereto, recording on the preceding paper sheet is not stopped. In this case, recording is stopped after image recording on the preceding paper sheet is completed.

Next, when image recording is stopped, all the inkjet heads 146C, 146M, 146Y, and 146K are simultaneously retreated from the inkjet recording drum 142 (step S13). As a consequence, it becomes possible to avoid the situation in which the paper sheet P having floating contacts the inkjet heads 146C, 146M, 146Y, and 146K.

Next, the image on the paper sheet P detected to have floating is read (step S14). The image in a fixed front and rear range in the conveyance direction is read with the floating detection position as a reference. The read image is then displayed on the display device 170 (step S15).

Thus, in the inkjet recording apparatus 100 of the present embodiment, when floating is detected on a paper sheet P by the inkjet recording unit 140, an image of the paper sheet P in a portion where floating is generated is read with the image reader 149, and the image is displayed on the display device 170. The operator can discriminate the type of the floating generated in the paper sheet P by visually confirming the display of the display device 170. As a consequence, an appropriate measure corresponding to the type of the floating can be taken. That is, since solutions to floating are different depending on the type of the floating, an appropriate measure can be taken when the type of the generated floating can be confirmed. Moreover, the displayed image is not the image of the entire paper sheet but the image of a portion where floating is generated, so that a floating generation position can easily be found out. Furthermore, since the image is read from part of the paper sheet, the processing load in reading operation can be reduced. As a consequence, the processing speed of the paper sheet P can be enhanced.

Since conveyance of the paper sheet P is not stopped even when floating is generated, generation of waste sheets can be suppressed, and the time taken for restart can be shortened. Note that it is preferable to stop feeding of the paper sheets P when floating is detected. In this way, generation of waste sheets can further be suppressed.

Since the image reader 149 is also used for defective nozzle detection and density unevenness detection, effective use of existing equipment can be achieved.

<<Modified Example of Reading>>

In the configuration of the above embodiment, when floating is detected in a paper sheet, the image in a fixed front and rear range is read with the position where the floating is detected as a reference. However, the form of reading is not limited thereto. It is possible to adopt the configuration in which the floating generation portion is read from part of the entire paper sheet.

<First Modification of Reading>

Figure 19:
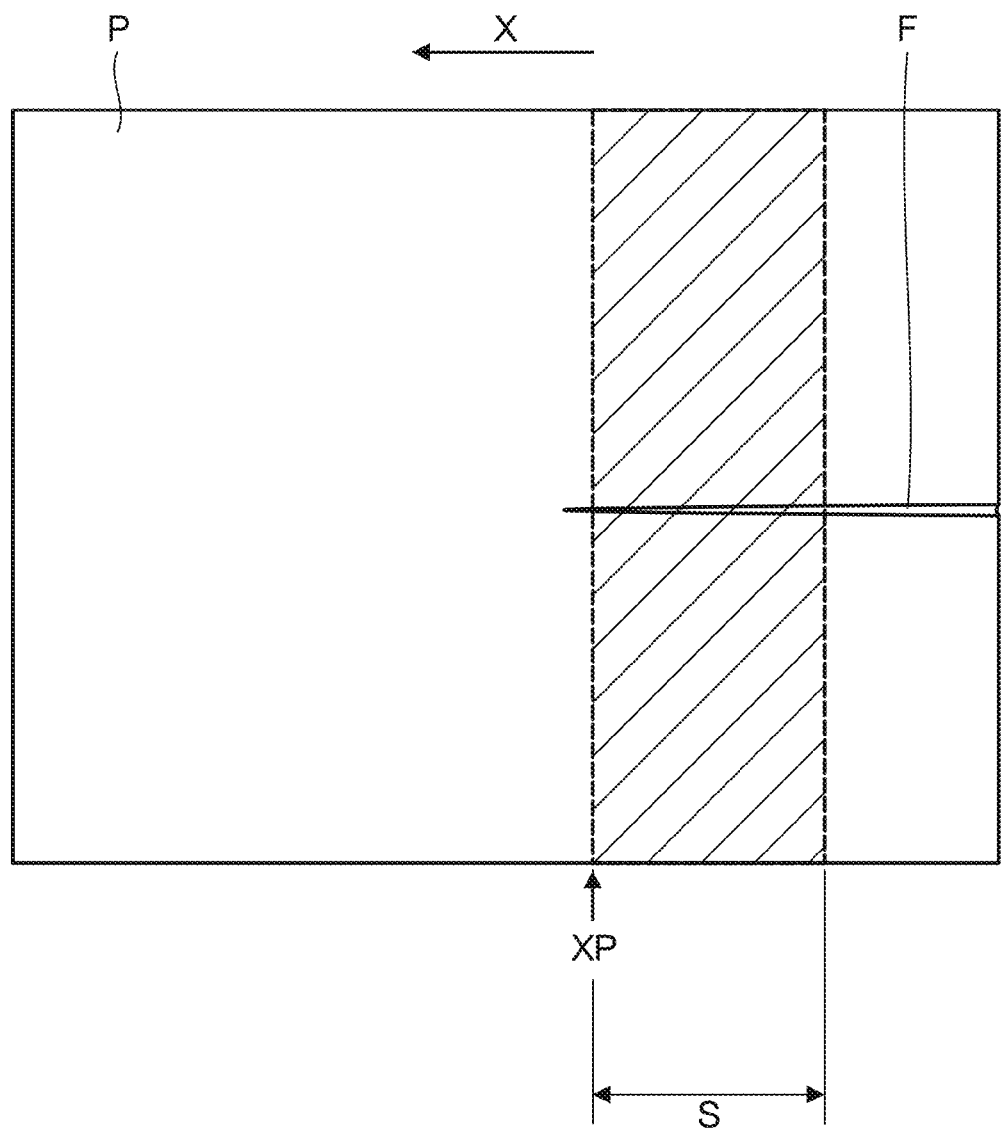
FIG. 19 is a concept view illustrating another example of image reading when floating is detected.

FIG. 19 is a concept view illustrating another example of image reading when floating is detected.

As illustrated in FIG. 19, a fixed rear range in the conveyance direction X of the paper sheet P may also be set as an image reading range S with the position XP where floating F is detected as a reference. When the fixed rear range is read in this way, an image can be read from part of the entire paper sheet by concentrating attention on the portion where the floating is generated.

In this case, when floating of the paper sheet P is detected by the paper floating detecting unit 147, the image reading control unit 240 controls driving of the image reader 149 so that the image in a fixed rear range in the conveyance direction of the paper sheet P is read with the floating detection position XP as a reference. Specifically, when floating is detected, driving of the image reader 149 is controlled so that reading is started after the lapse of prescribed time from the detection, and reading is finished after the lapse of prescribed time from the start of reading.

The image reading range is set to be the range that is a part in the conveyance direction of the paper sheet P which is at least large enough to enable the type of the floating to be discriminated from the read image. The type of the floating can also be discriminated from an image showing part of the floating. Therefore, it is not necessary required to read the entire range of the generated floating. For example, as illustrated in FIG. 17, floating such as floating caused by a longitudinal wrinkle can be discriminated from the image showing only part thereof.

<Second Modification of Reading>

Figure 20:
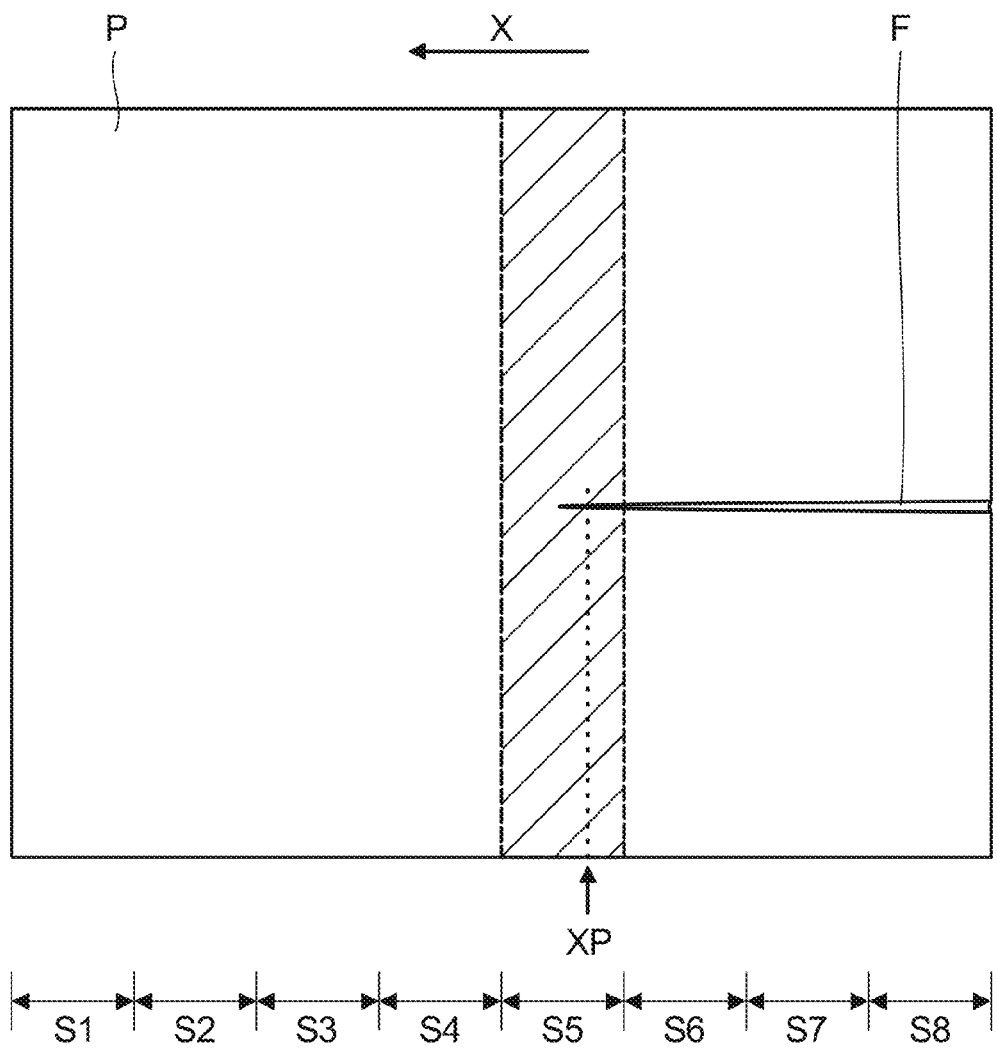
FIG. 20 is a concept view illustrating another example of image reading when floating is detected.

FIG. 20 is a concept view illustrating another example of image reading when floating is detected.

As illustrated in FIG. 20, the paper sheet P may be divided into a plurality of regions S1, S2, . . . along the conveyance direction X of the paper sheet P, and a region detected to include floating F may be set as an image reading range. In the example illustrated in FIG. 20, the floating F is detected in a region S5, so that the region S5 is set as the read region.

The number of the regions to be divided can properly be set in accordance with the size of the paper sheet P or the like. Although only the region where the floating F is detected is set as the image reading range in the aforementioned example, the floating F detection region and a fixed front and rear region of the floating F detection region may be set as the image reading range. Or the floating F detection region and a fixed rear region of the floating F detection region may be set as the image reading range.

<<Modified Example of Displaying Read Image>>

In the above embodiment, the image read with the image reader 149 is displayed on the display device 170 without any other reprocessing. However, the processing of emphasizing the floating generated in the paper sheet may be applied to the image, and the processed image may be displayed on the display device 170.

Figure 21:
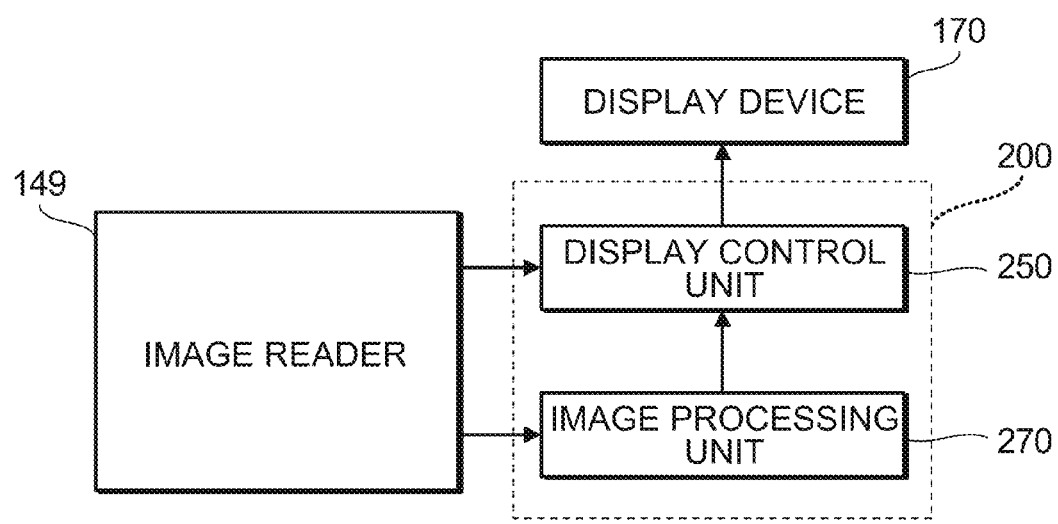
FIG. 21 is a functional block diagram of the computer in the case of image-processing and displaying a read image.

FIG. 21 is a functional block diagram of the computer in the case of image-processing and displaying a read image.

The computer 200 executes a specified program to implement the function of the image processing unit 270.

The image processing unit 270 acquires image data from the image reader 149, and applies the processing of emphasizing the floating generated in a paper sheet to the image data. For example, the image processing is the processing of emphasizing contrast.

The display control unit 250 acquires the image data image-processed in the image processing unit 270, and displays the image data on the display device 170.

Thus, the read image is subjected to the processing of emphasizing floating and is then displayed on the display device 170. Accordingly, when confirming the type of the floating based on the image displayed on the display device 170, the operator can easily confirm the type of the floating.

Figure 22A:
FIG. 22A is an image of floating actually generated on an inkjet recording drum, the image being taken with a digital camera.
Figure 22B:
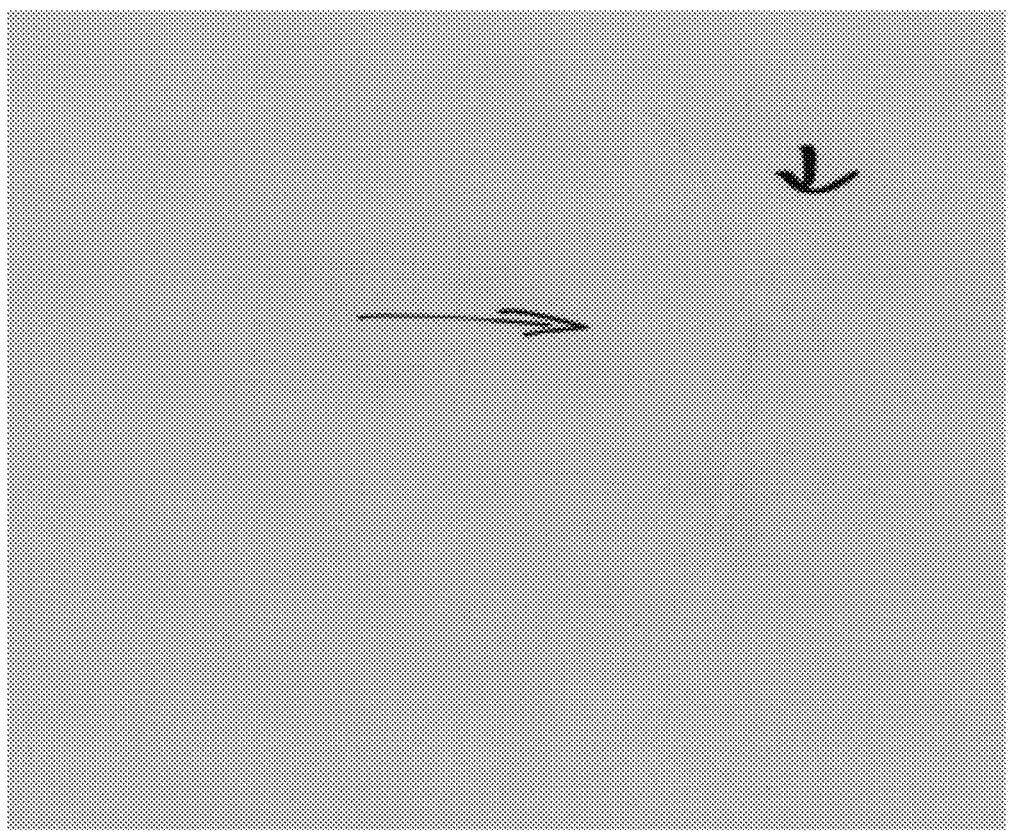
FIG. 22B is an image of a paper sheet illustrated in FIG. 22A, the image being read with an image reader.
Figure 22C:
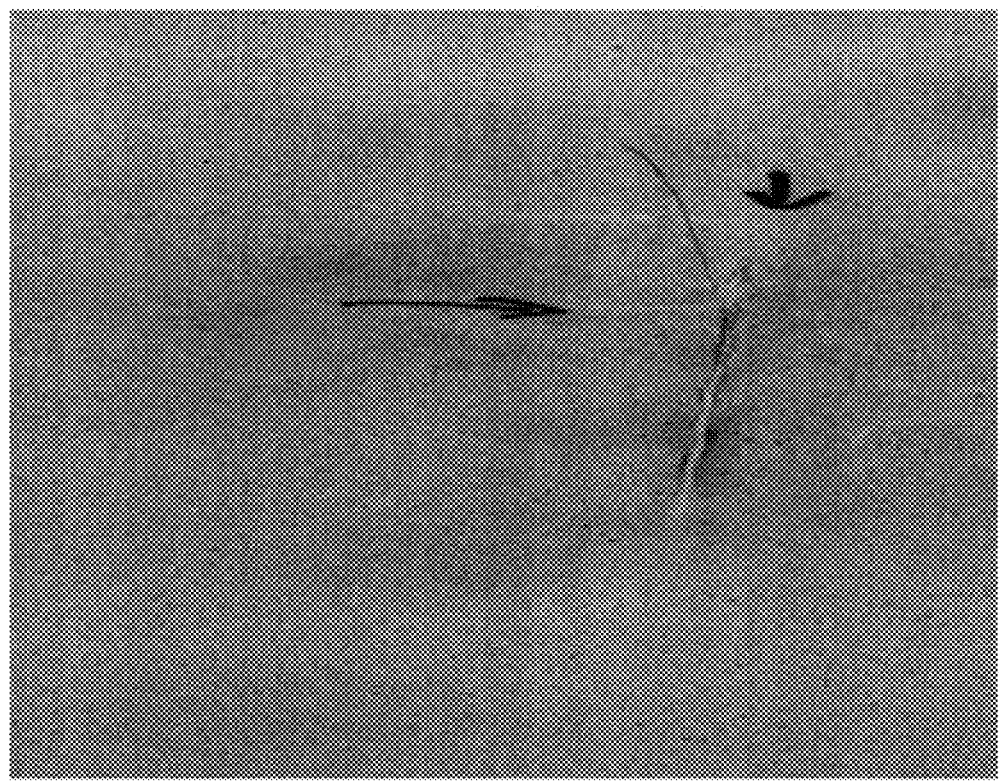
FIG. 22C is an image obtained by applying processing of emphasizing contrast to the image illustrated in FIG. 22B.

FIG. 22A is an image of floating actually generated on the inkjet recording drum, the image being taken with a digital camera. FIG. 22A illustrates the example in which floating is generated due to a longitudinal wrinkle. Arrows in the image are directly written on the paper sheet with a pen to indicate the position where the floating is generated. FIG. 22B is an image of the paper sheet illustrated in FIG. 22A, the image being read with the image reader. FIG. 22C is an image obtained by applying processing of emphasizing contrast to the image illustrated in FIG. 22B. As illustrated in FIG. 22C, the processing of emphasizing contrast is applied to emphasize the floating, so that the floating can easily be confirmed from the image.

Figure 23A:
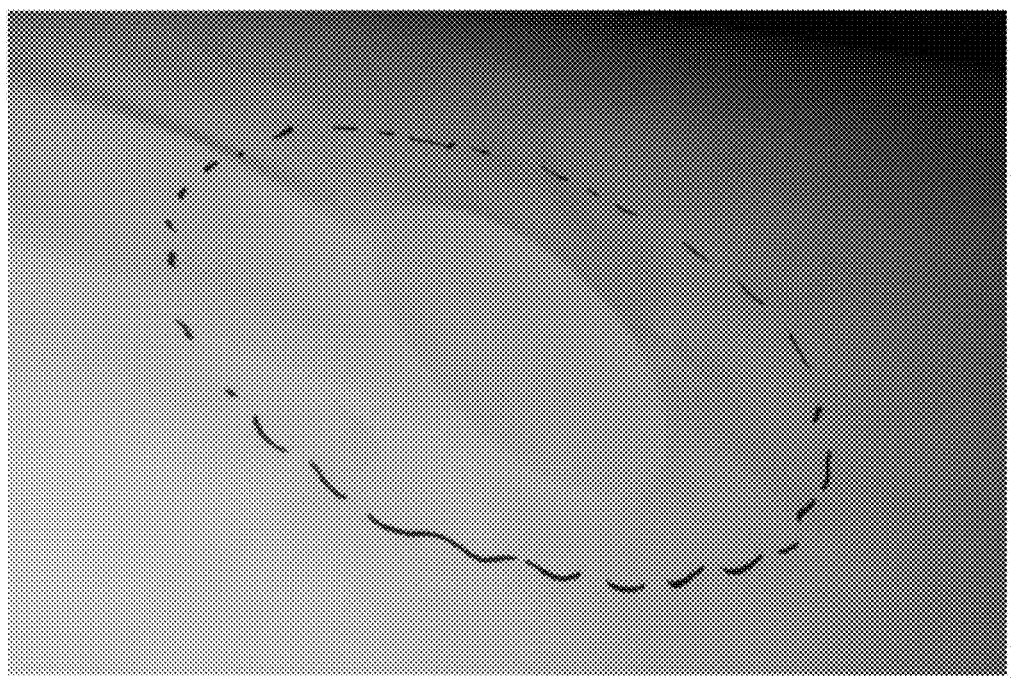
FIG. 23A is an image of floating actually generated on the inkjet recording drum, the image being taken with the digital camera.
Figure 23B:
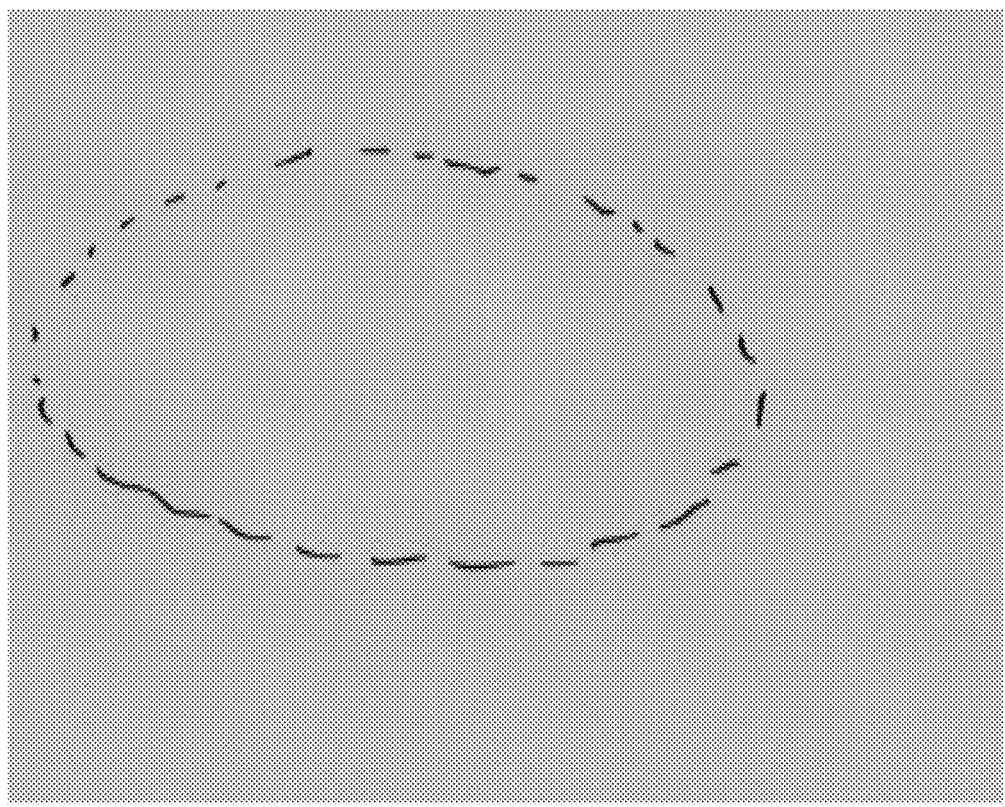
FIG. 23B is an image of a paper sheet illustrated in FIG. 23A, the image being read with the image reader.
Figure 23C:
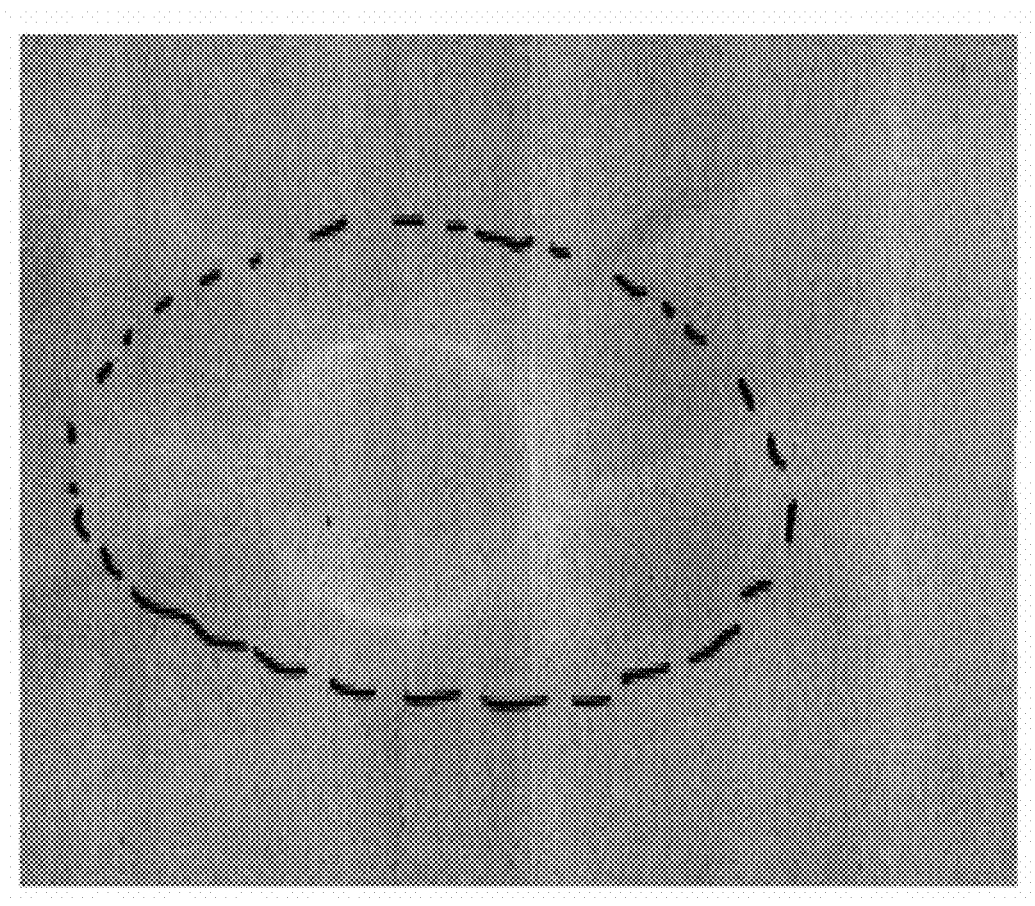
FIG. 23C is an image obtained by applying processing of emphasizing contrast to the image illustrated in FIG. 23B.

Like FIG. 22A, FIG. 23A is an image of floating actually generated on the inkjet recording drum, the image being taken with the digital camera. The example illustrated in FIG. 23A indicates the case where floating is generated due to an annular wrinkle. A broken line circle illustrated in the image is directly written on the paper sheet with a pen to indicate the position where the floating is generated. FIG. 23B is an image of a paper sheet illustrated in FIG. 23A, the image being read with the image reader. FIG. 23C is an image obtained by applying processing of emphasizing contrast to the image illustrated in FIG. 23B. As illustrated in FIG. 23C, the processing of emphasizing contrast is applied to emphasize the floating, so that the floating can easily be confirmed from the image.

By applying the processing of emphasizing floating in this way, the floating can easily be confirmed from the read image. The imaging processing for emphasizing the floating is not particularly limited. Processing such as edge emphasis processing other than the processing of emphasizing contrast may also be adopted.

Instead of the configuration in which the image-processed image is always displayed, the configuration in which image processing is executed in response to an instruction from the operator, and an image after the image processing is displayed on the display device 170 may also be adopted.

It is also possible to adopt the configuration in which an image-processed image and an unprocessed image are simultaneously displayed, or the configuration in which the image-processed image and the unprocessed image are switched and displayed.

<<Second Embodiment>>

In an inkjet recording apparatus of the present embodiment, an image of the paper sheet read with the image reader is analyzed by a computer, and the type of floating is automatically discriminated. Since the configuration of reading an image on the paper sheet having floating is the same as the configuration of the inkjet recording apparatus described before, only the configuration of automatically discriminating the type of the generated floating is described herein.

The inkjet recording apparatus of the present embodiment includes a paper sheet floating type discriminating unit 300 which discriminates the type of the floating generated in the paper sheet based on the image read with the image reader. The computer 200 executes a specified program to implement a function as the paper sheet floating type discriminating unit 300.

Figure 24:
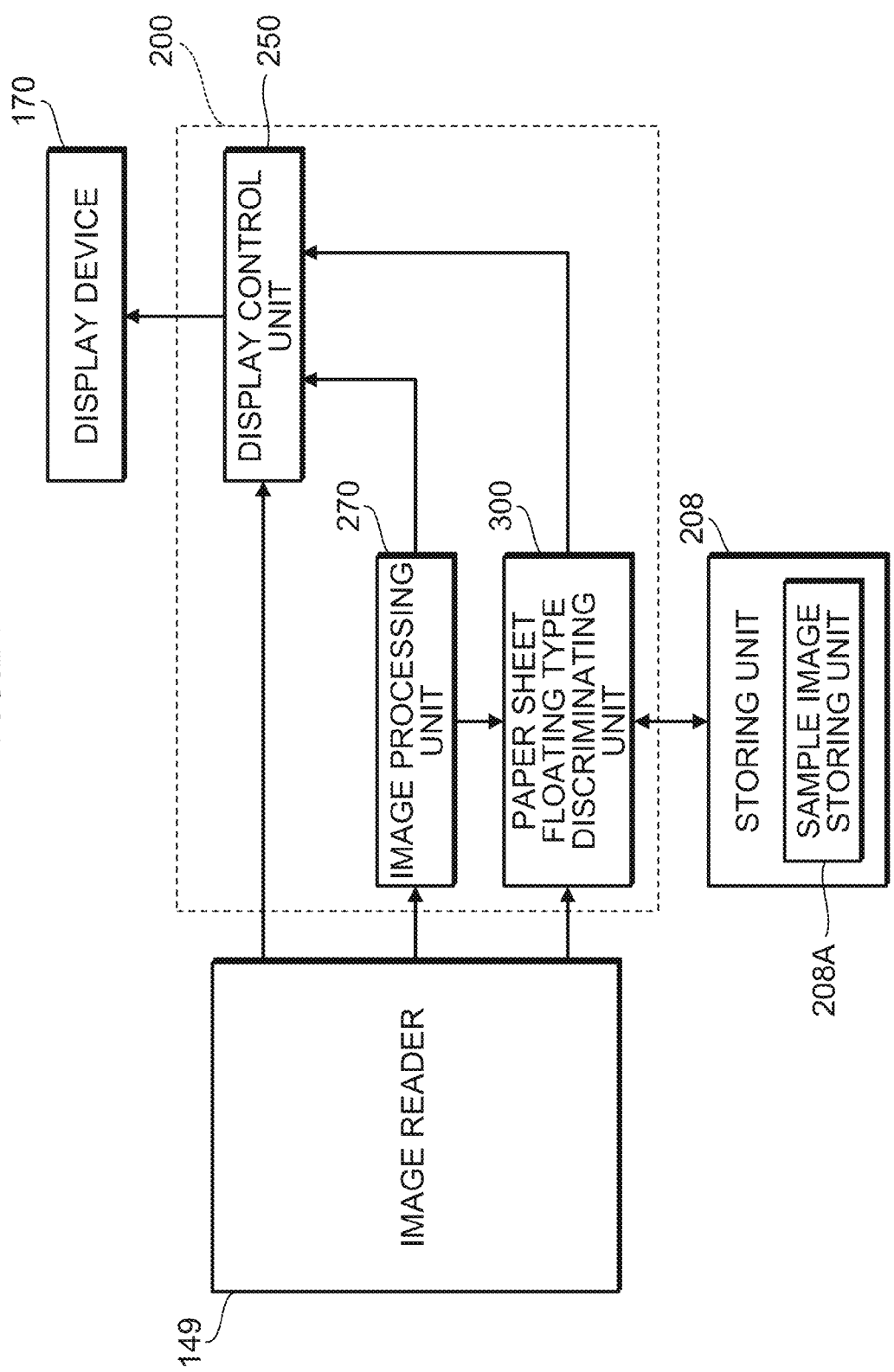
FIG. 24 is a functional block diagram of the computer which functions as a paper sheet floating type discriminating unit.

FIG. 24 is a functional block diagram of the computer which functions as the paper sheet floating type discriminating unit.

The paper sheet floating type discriminating unit 300 acquires an image read with the image reader 149 and analyzes the acquired image to discriminate the type of the floating generated in the paper sheet P. The display control unit 250 acquires information about the result of discrimination by the paper sheet floating type discriminating unit 300, and displays the information on the display device 170.

<Method for Discriminating Paper Sheet Floating Type>

The paper sheet floating type discriminating unit 300 analyzes an image read with the image reader 149, and discriminates the type of the floating generated in the paper sheet P. Hereinafter, the discriminating method is described.

(A) Method for discriminating the type of floating generated in a paper sheet based on brightness change in an image in the paper width direction, the image being read with the image reader The paper width direction is a direction orthogonal to the conveyance direction X of the paper sheet P.

When an image on the paper sheet without floating is read with the image reader 149, the brightness change in the paper width direction is substantially zero.

In the case of the paper sheet with floating, a light reflection state changes in the floating portion. Accordingly, when the image thereon is read with the image reader 149, the brightness changes in the floating portion. Therefore, by identifying the position where the brightness changes, the position where floating is generated can be identified.

Since the light reflection is different depending on the state of floating, the type of floating can be identified by identifying the mode of brightness change.

Figure 25A:
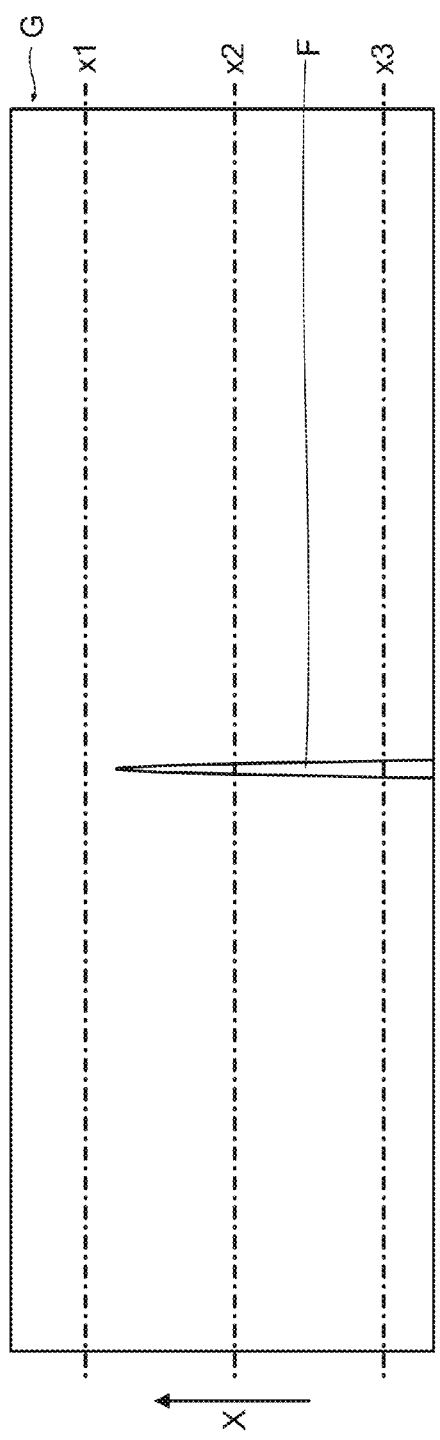
FIGS. 25A to 25D are concept views in the case of detecting a longitudinal wrinkle based on brightness change.
Figure 25B:
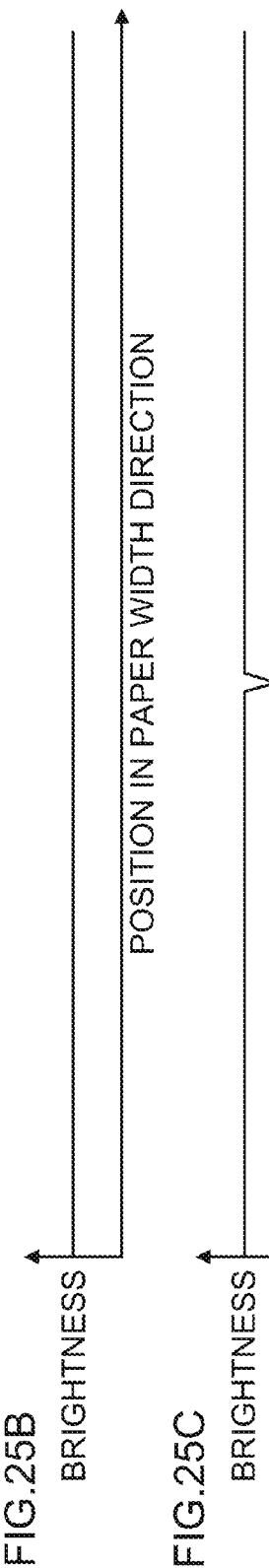
Figure 25C:
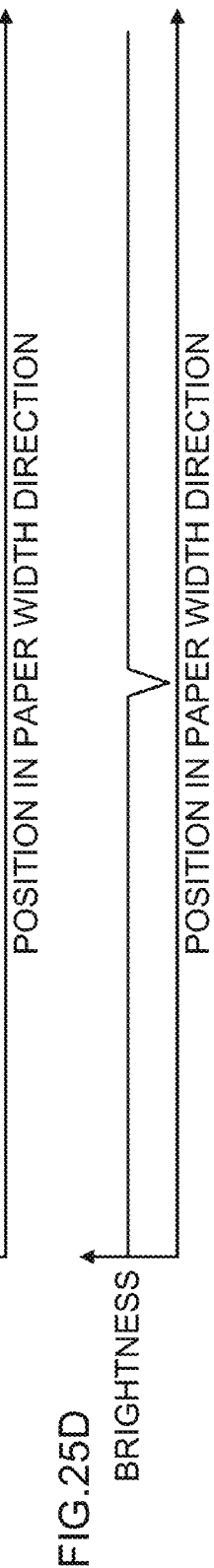
Figure 25D:

FIGS. 25A to 25D are concept views in the case of detecting a longitudinal wrinkle based on the brightness change. FIG. 25A illustrates an image on a paper sheet having a longitudinal wrinkle, the image being read with an image reader. FIGS. 25B to 25D are graph views illustrating brightness change at positions x1, x2, and x3 of the read image illustrated in FIG. 25A, respectively.

As illustrated in FIG. 25B, the brightness change in the paper width direction is substantially zero at the position without floating. On the contrary, at the positions with floating as illustrated in FIGS. 25C and 25D, the brightness changes at the position where the floating is present. The brightness change varies in accordance with the width of the wrinkle.

Since the longitudinal wrinkle is a linear wrinkle, the brightness change appears at substantially the same position in the paper width direction. When such a brightness change is detected from the image, it can be estimated that the type of the floating is a longitudinal wrinkle.

FIGS. 26A to 26D are concept views in the case of detecting an annular wrinkle based on the brightness change. FIG. 26A illustrates an image on a paper sheet having an annular wrinkle, the image being read with the image reader. FIGS. 26B to 26D are graph views illustrating brightness change at positions x1, x2, and x3 of the read image illustrated in FIG. 26A, respectively.

As illustrated in FIGS. 26B to 26D, brightness change appears at two positions in the paper width direction in the case of the annular wrinkle. Also in the case of the annular wrinkle, the generation position changes in the conveyance direction X of the paper sheet P. When such a brightness change is detected from the image, it can be estimated that the type of the floating is an annular wrinkle.

The annular wrinkle has a characteristic of having a width W larger than that of the longitudinal wrinkle, the width W being the width of a portion having a brightness change. Therefore, when such a characteristic is detected, it can be estimated that the type of floating is an annular wrinkle.

Thus, the type of the floating generated in the paper sheet P can be discriminated based on the brightness change in the image in the paper width direction, the image being read with the image reader 149.

The paper sheet floating type discriminating unit 300 acquires an image read with the image reader 149 and analyzes the acquired image to discriminate the type of the floating generated in the paper sheet P based on the brightness information.

(B) Method for discriminating the type of floating generated in a paper sheet by utilizing pattern matching The type of the floating generated in the paper sheet can be discriminated by pattern matching with sample images prepared in advance.

The types of the floating generated in the paper sheet, such as wrinkles and folding, are limited to some extent. Accordingly, two or more kinds of sample images are prepared for each type, and pattern matching with these sample images is performed to determine the type of the floating of the read image. Specifically, correlation coefficients with the respective sample images are calculated, and the type of floating of a sample image with the highest correlation coefficient is regarded as the type of floating of the read image.

As described in the foregoing, two or more kinds of sample images are prepared for each type. The sample images are stored in the storing unit 208. The storing unit 208 is one example of a storing device which functions as a sample image storing unit 208A.

The paper sheet floating type discriminating unit 300 acquires an image read with the image reader 149 and discriminates the type of floating generated in the paper sheet by pattern matching with the sample images stored in the storing unit 208. The sample images are subjected to expansion or reduction processing as necessary, and are then used for the matching processing.

FIG. 27 is a flow chart illustrating one example of processing procedures in the case of discriminating the type of floating by pattern matching.

First, a sample image is acquired (step S20). Sample images are read in a preset order.

Next, an average brightness of the acquired sample image is adjusted to an average brightness of a read image (step S21). In this case, precision can be enhanced by using the average brightness of a region without floating. This is because only the whiteness of the paper sheet is theoretically present in the region without floating.

Next, a similarity R between the read image and the sample image is calculated by a following expression, where I(i, j) represents a brightness value of each pixel of the read image and T(i, j) represents a brightness value of each pixel of the sample image (step S22):

$$R = \frac{\sum_{j=0}^{N-1}\sum_{i=0}^{M-1} I(i,j)T(i,j)}{\sqrt{\sum_{j=0}^{N-1}\sum_{i=0}^{M-1} I(i,j)^2 \times \sum_{j=0}^{N-1}\sum_{i=0}^{M-1} T(i,j)^2}}$$ [Expression 1]

Here, when the sample image has a width of m pixels and a height of n pixels, an upper left corner (or lower left corner) has coordinates of (0, 0), and a lower right corner (or upper right corner) has coordinates of (m-1, n-1).

Next, it is determined whether or not the calculated similarity R is equal to or more than a threshold (step S23). To set a stricter similarity determination criterion, a larger value is set as the threshold. For example, a value of 0.3 to 0.5 is set as the threshold.

When the similarity R is equal to or more than the threshold as a result of determination, the type of the floating into which the sample image is classified is determined as the type of the floating of the read image (step S24), and the processing is ended.

When the similarity R is less than the threshold as a result of determination, the presence/absence of a subsequent sample image is determined (step S25). When the subsequent sample image to be compared is present, the sample image is read, and the processing from the steps S20 to S23 is carried out.

Contrary to this, when the subsequent sample image to be compared is not present, that is, when comparison with all the sample images is finished, it is determined that determination is impossible (step S26), and processing is ended.

Thus, by performing pattern matching with the sample images prepared in advance, the type of floating generated in the paper sheet can be discriminated.

(C) Method for detecting floating of location dependence type

FIGS. 28A and 28B illustrate a read image of a paper sheet without floating and a read image of a paper sheet having floating caused by folding. FIG. 28A illustrates the read image of the paper sheet without floating, and FIG. 28B illustrates the read image of the paper sheet having floating caused by folding V.

The floating due to folding has location dependence and is therefore always generated at the end of the paper sheet. In the case of the floating which has location dependence, such as floating due to folding, the type of floating can easily be discriminated based on the premise that "every paper sheet has a square shape constituted of four straight lines."

That is, when folding is generated in a certain corner, the image of the paper sheet loses its square shape. Accordingly, it becomes possible to discriminate whether folding is generated or not by determining whether or not the read image has a square shape.

Since the read image is part of a paper sheet, actually, an edge portion is extracted from the read image, and whether or not the extracted edge portion is constituted of straight lines is determined to detect whether or not folding is generated. Or a corner portion is extracted from the read image, and whether or not the extracted corner portion is at right angles is determined to detect whether or not folding is generated.

Detection of folding can be used together with the analysis based on brightness or the analysis by pattern matching described before. For example, it is possible to adopt the configuration in which detection of folding is carried out first, and then the analysis based on brightness or analysis by pattern matching is carried out if folding is not detected. In this case, it is also possible to adopt the configuration of carrying out detection of folding only when floating is detected at the end of the paper sheet.

<Display of Discrimination Result>

The result of discrimination by the paper sheet floating type discriminating unit 300 is displayed on the display device 170. The display control unit 250 acquires information about the result of discrimination by the paper sheet floating type discriminating unit 300, and displays the information on the display device 170.

In addition to the information on the discriminated type of the paper sheet floating, the image read with the image reader 149 may also be displayed. In this case, the image may be subjected to the processing of emphasizing the floating and then be displayed.

<<Third Embodiment>>

When floating of a paper sheet is detected, a conveyance system and/or a paper feeding system are adjusted. Adjustment needs to be performed in accordance with the type of the generated floating.

In the inkjet recording apparatus of the present embodiment, the type of floating is discriminated from the image read with the image reader, and a solution corresponding to the type of the generated floating is presented.

Since the method for discriminating the type of floating is the same as that in the second embodiment, a method for presenting the solution to the floating is described herein.

The inkjet recording apparatus includes a solution searching unit 310 which searches for the solution to the floating with reference to a specified database.

FIG. 29 is a functional block diagram of the computer which functions as the solution searching unit.

The storing unit 208 connected to the computer 200 stores information on the solution to each type of the floating generated in the paper sheet P as a solution database. The storing unit 208 is one example of the storing device which functions as a solution storing unit 208B.

FIG. 30 is a table illustrating one example of the solution database. As illustrated in FIG. 30, the solution to each type of floating is registered into the solution database.

The solution searching unit 310 acquires the information on the type of the generated floating from the paper sheet floating type discriminating unit 300, and searches the solution database for the solution to the floating.

The information on the solution searched for by the solution searching unit 310 is displayed on the display device 170. The display control unit 250 acquires the information on the solution searched for by the solution searching unit 310, and displays the information on the display device 170.

In addition to the information on the solution, the information on the type of the floating discriminated by the paper sheet floating type discriminating unit 300 may also be displayed. The image read with the image reader 149 may further be displayed. When the image read with the image reader 149 is displayed, the image may be subjected to the processing of emphasizing floating and then be displayed.

FIG. 31 illustrates an example of a solution to floating displayed on the display device. In this example, information on the type of generated floating and an image G read with the image reader 149 are displayed together with the information on the solution. A setting screen corresponding to the solution is displayed. FIG. 31 is one example in which folding is generated.

Presenting the solution in this way enables anyone to easily take an appropriate measure without the necessity of the knowledge of a skilled operator.

<<Fourth Embodiment>>

In an inkjet recording apparatus of the present embodiment, the type of floating is discriminated from an image read with the image reader, a solution thereto is searched for, and feed and/or conveyance of the paper sheet is automatically adjusted.

The method for discriminating the type of floating from the image read with the image reader and searching for the solution thereto is the same as that in the inkjet recording apparatus in each of the embodiments described before. Accordingly, only a method for automatically adjusting the feed and/or conveyance of the paper sheet is described herein.

The inkjet recording apparatus includes an automatic adjusting unit 320 which automatically adjusts feed and/or conveyance of the paper sheet based on the solution searched for by the solution searching unit 310. The computer 200 executes a specified program to implement the function of the automatic adjusting unit 320. The automatic adjusting unit 320 is one example of the adjusting device.

Figure 32:
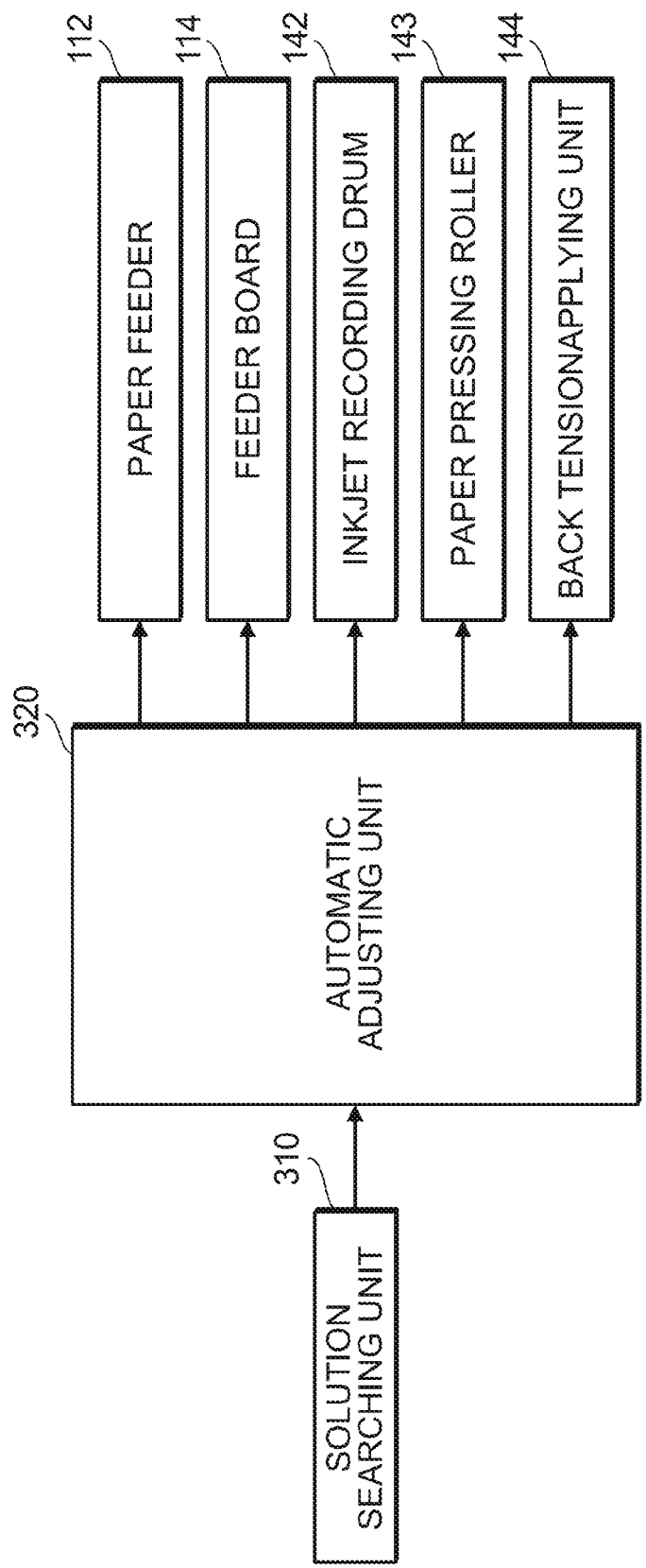
FIG. 32 is a functional block diagram of the computer which functions as an automatic adjusting unit.

FIG. 32 is a functional block diagram of the computer which functions as the automatic adjusting unit.

The automatic adjusting unit 320 acquires information on the solution searched for by the solution searching unit 310, and automatically adjusts setting of feed and conveyance. For example, based on the acquired information on the solution, volume of air from the blower is automatically adjusted for the paper feeder 112. Based on the acquired information on the solution, the position of the retainer 114C in the feeder board 114 is also automatically adjusted. Based on the acquired information on the solution, the position of the runner wheel 114A in the feeder board 114 is also automatically adjusted. Based on the acquired information on the solution, the sucking pressure of the inkjet recording drum 142 is also automatically adjusted. Based on the acquired information on the solution, the pressing force of the paper pressing roller 143 is also automatically adjusted. Based on the acquired information on the solution, the sucking pressure of the back tension applying unit 144 is also automatically adjusted.

When floating is detected, the solution thereto is automatically searched for, and feed and/or conveyance is automatically adjusted. As a result, automatic restart of operation can be achieved without human assistance.

When floating is detected, the forward/backward movement control unit 260 retreats the inkjet heads 146C, 146M, 146Y, and 146K. However, when floating of the paper sheet P is no longer detected by the paper floating detecting unit 147 after restart of operation, the forward/backward movement control unit 260 returns the inkjet heads 146C, 146M, 146Y, and 146K to the positions before retreat. As a consequence, operation can be resumed safely. This also applies to the case where manual adjustment is performed.

<<Other Embodiments>>

According to the above-disclosed embodiments, the paper sheet is conveyed by the drum in the inkjet recording unit. However, the conveying device of the paper sheet is not limited thereto. The above configuration may be replaced by the configuration of conveying the paper sheet by sucking the paper sheet to a running belt. Or the configuration of conveying the paper sheet on a platen with a roller may also be adopted. In the case of conveying with a belt, floating-up of a certain level or more of the paper sheet is detected with the surface of the belt as a reference, the surface being a suction holding surface. In the case of conveying with a roller, floating-up of a certain level or more from the platen is detected as floating.

The solution database is prepared in conformity with the configuration of the paper feeding system and the conveyance system of the inkjet recording apparatus.

The automatic adjustment is also performed in conformity with the configuration of the paper feeding system and the conveyance system of the inkjet recording apparatus.

The paper sheets include sheet-like media at large which are used as recording objects of the inkjet recording apparatus. Therefore, sheets made of resin, such as transparent sheets for overhead projectors, are also embraced in the concept of the paper sheets of the present invention.

What is claimed is:

1. An inkjet recording apparatus, comprising:
   a conveying device which conveys a paper sheet along a fixed conveying path;
   a paper sheet floating detecting device which detects floating of the paper sheet conveyed by the conveying device at a first position set on the conveying path;
   an ink jet recording device which records an image on the paper sheet conveyed by the conveying device at a second position set on a downstream side of the first position;
   an image reading device which reads, line by line, the image of the paper sheet conveyed by the conveying device at a third position set on the downstream side of the second position; and
   an image reading control unit which makes the image reading device read the image in a fixed range along a conveyance direction of the paper sheet when the floating of the paper sheet is detected by the paper sheet floating detecting device, the image being read with a position where the floating is detected as a reference.

2. The inkjet recording apparatus according to claim 1, wherein when the floating of the paper sheet is detected by the paper sheet floating detecting device, the image reading control unit makes the image reading device read the image in a fixed front and rear range in the conveyance direction of the paper sheet with the position where the floating is detected as a reference.

3. The inkjet recording apparatus according to claim 1, wherein when the floating of the paper sheet is detected by the paper sheet floating detecting device, the image reading control unit makes the image reading device read the image in a fixed rear range in the conveyance direction of the paper sheet with the position where the floating is detected as a reference.

4. The inkjet recording apparatus according to claim 1, further comprising:
a display device; and
a display control unit which makes the display device display the image read by the image reading device.

5. The inkjet recording apparatus according to claim 1, further comprising:
an image processing unit which applies processing of emphasizing the floating generated in the paper sheet to the image read by the image reading device;
a display device; and
a display control unit which makes the display device display the image processed by the image processing unit.

6. The inkjet recording apparatus according to claim 1, further comprising:
a paper sheet floating type discriminating unit which analyzes the image read by the image reading device to discriminate a type of the floating generated in the paper sheet;
a display device; and
a display control unit which makes the display device display information on the type of the floating discriminated by the paper sheet floating discriminating unit.

7. The inkjet recording apparatus according to claim 6, further comprising
a sample image storing unit which stores a sample image for each type of the floating generated in the paper sheet,
wherein the paper sheet floating type discriminating unit discriminates the type of the floating generated in the paper sheet by pattern matching with the sample images stored in the sample image storing unit.

8. The inkjet recording apparatus according to claim 6,
wherein the paper sheet floating type discriminating unit discriminates the type of the floating generated in the paper sheet based on brightness change in the image in a paper width direction, the image being read by the image reading device.

9. The inkjet recording apparatus according to claim 1, further comprising:
a paper sheet floating type discriminating unit which analyzes the image read by the image reading device to discriminate a type of the floating generated in the paper sheet;
a solution storing unit which stores information on a solution to each type of the floating generated in the paper sheet;
a solution searching unit which searches for the solution corresponding to the type of the floating discriminated by the paper sheet floating type discriminating unit with reference to the information stored in the solution storing unit;
a display device; and
a display control unit which makes the display device display information on the solution searched for by the solution searching unit.

10. The inkjet recording apparatus according to claim 1, further comprising:
a paper sheet floating type discriminating unit which analyzes the image read by the image reading device to discriminate a type of the floating generated in the paper sheet;
a solution storing unit which stores information on a solution to each type of the floating generated in the paper sheet;
a solution searching unit which searches for the solution corresponding to the type of the floating discriminated by the paper sheet floating type discriminating unit with reference to the information stored in the solution storing unit; and
an adjusting device which automatically adjusts feed and/or conveyance of the paper sheet based on the solution searched for by the solution searching unit.

11. The inkjet recording apparatus according to claim 1, further comprising
a forward/backward moving device which moves the ink jet recording device forward and backward; and
a forward/backward movement control unit which controls the forward/backward moving device to retreat the ink jet recording device when the floating of the paper sheet is detected by the paper sheet floating detecting device.

12. The inkjet recording apparatus according to claim 11,
wherein when the floating of the paper sheet is no longer detected by the paper sheet floating detecting device after the ink jet recording device is retreated, the forward/backward movement control unit returns the ink jet recording device to a position before retreat.

13. The inkjet recording apparatus according to claim 1, further comprising
an image recording stop control unit which makes the ink jet recording device stop recording of the image when the floating of the paper sheet is detected by the paper sheet floating detecting device.

\* \* \* \* \*